(12) United States Patent
Bebawy et al.

(10) Patent No.: US 11,448,649 B2
(45) Date of Patent: Sep. 20, 2022

(54) METHOD FOR CANCER PROGNOSIS

(71) Applicant: UNIVERSITY OF TECHNOLOGY SYDNEY, Broadway (AU)

(72) Inventors: Mary Bebawy, Broadway (AU); Sabna Rajeev Krishnan, Broadway (AU)

(73) Assignee: UNIVERSITY OF TECHNOLOGY SYDNEY, Broadway (AU)

( * ) Notice: Subject to any disclaimer, the term of this patent is extended or adjusted under 35 U.S.C. 154(b) by 440 days.

(21) Appl. No.: 16/610,901

(22) PCT Filed: May 7, 2018

(86) PCT No.: PCT/AU2018/050420
§ 371 (c)(1),
(2) Date: Nov. 4, 2019

(87) PCT Pub. No.: WO2018/201206
PCT Pub. Date: Nov. 8, 2018

(65) Prior Publication Data
US 2020/0158730 A1    May 21, 2020

(30) Foreign Application Priority Data

May 5, 2017 (AU) ................. 2017901660

(51) Int. Cl.
*G01N 33/574* (2006.01)
*G01N 33/50* (2006.01)
*C12N 5/09* (2010.01)

(52) U.S. Cl.
CPC ... *G01N 33/57407* (2013.01); *G01N 33/5091* (2013.01); *C12N 5/0694* (2013.01); *G01N 2333/70596* (2013.01)

(58) Field of Classification Search
CPC ..... G01N 2333/70596; G01N 2800/44; G01N 2800/52; G01N 33/5091; G01N 33/57407; G01N 33/57426; G01N 33/57484; G01N 33/6872; G01N 33/5076; C12N 5/0694
See application file for complete search history.

(56) References Cited

FOREIGN PATENT DOCUMENTS

| | | |
|---|---|---|
| JP | 2004-504816 A | 2/2004 |
| JP | 2007-521831 A | 8/2007 |
| JP | 2011-509245 A | 3/2011 |
| WO | WO 2001/92877 A2 | 12/2001 |
| WO | WO 2005/083061 A1 | 9/2005 |
| WO | WO 2009/080829 A1 | 7/2009 |
| WO | WO 2017/072716 A1 | 5/2017 |

OTHER PUBLICATIONS

European Search Report for European Application No. EP 18793974.9, 11 pages, dated Dec. 2, 2020.

(Continued)

*Primary Examiner* — Jennifer Wecker
*Assistant Examiner* — Kathryn Elizabeth Limbaugh
(74) *Attorney, Agent, or Firm* — Squire Patton Boggs (US) LLP

(57) ABSTRACT

The present invention relates to methods of prognosing and monitoring cancer using circulating cells and/or extracellular vesicles as indicators of the progression of plasma cell neoplasms in patients.

20 Claims, 6 Drawing Sheets

(56) References Cited

OTHER PUBLICATIONS

Surman Magdalena et al: "Deciphering the role of ectosomes in cancer development and progression: focus on the proteome", PLOS Biology, Rapid Science Publishers, Dordrecht, vol. 34, No. 3, Mar. 19, 2017 (Mar. 19, 2017), pp. 273-289, XP036242864, ISSN: 0262-0898, DOI: 10.1007/S10585-017-9844-Z [retrieved on Mar. 19, 2017].

Sabna Rajeev Krishnan et al: "A liquid biopsy to detect multidrug resistance and disease burden in multiple myeloma", Blood Cancer Journal, vol. 10, No. 3, Mar. 1, 2020 (Mar. 1, 2020), XP055752341, DOI: 10.1038/s41408-020-0304-7.

International Search Report and Written Opinion dated Jul. 2, 2018, in International Patent Application No. PCT/AU2018/050420, 8 pages.

Hawley et al., "Identification of an ABCB1 (P-glycoprotein)-positive carfilzomib-resistant myeloma subpopulation by the pluripotent stem cell fluorescent dye CDy1", Am J Hematol. Apr. 2013; 88(4): 265-272. Epub Mar. 8, 2013.

Liu et al., "Microvesicles secreted from human multiple myeloma cells promote angiogenesis", Acta Pharmacol Sin. Feb. 2014; 35(2): 230-238. Epub Dec. 30, 2013.

Loh et al., "Presence of Hoechst low side populations in multiple myeloma", Leuk Lymphoma. Sep. 2008; 49(9): 1813-1816.

Matsui et al., "Clonogenic Multiple Myeloma Progenitors, Stem Cell Properties, and Drug Resistance", Cancer Res. Jan. 1, 2008; 68(1): 190-197.

Rajeev Krishnan et al., "Isolation of Human CD138(+) Microparticles from the Plasma of Patients with Multiple Myeloma", Neoplasia. Jan. 2016; 18(1): 25-32.

English translation of Japanese Office Action for Japanese Patent Application No. 2019-560647, 3 pages, dated Mar. 17, 2022.

Bebawy M. et al., "Membrane microparticles mediatetransfer of P-glycoprotein to drug sensitive cancer cells", Apr. 16, 2009, Leukemia, vol. 23, pp. 1643-1649.

| Patient | Age (yrs.) | Gender | Response state | Total MP count (CD41a⁻) | CD41a⁻ | | | | | | | | |
|---|---|---|---|---|---|---|---|---|---|---|---|---|---|
| | | | | | CD138⁻ | | | | | | CD138⁺ | | |
| | | | | | P-gp⁺ (µl) | CD34⁺ (µl) | P-gp⁺CD34⁻ (µl) | P-gp⁻CD34⁺ (µl) | P-gp⁻CD34⁻ (µl) | P-gp⁺CD34⁺anxn V⁺ (µl) | P-gp⁺CD34⁻ (µl) | P-gp⁻CD34⁺ (µl) | P-gp⁺CD34⁺ (µl) | P-gp⁺CD34⁺ anxn V⁺ (µl) |
| Patient 1 | 58 | F | PD aggressive | 155.2 | 496.81 | 12.5 | 28.5 | 56.4 | 5 | 0.3 | 0.3 | 0 | 0 |
| Patient 2 | 66 | F | PD | 60 | 40.5 | 4.78 | 74 | 60 | 1.1 | 0.5 | 5 | 3 | 0.4 |
| Patient 3 | 63 | M | Stable | 6.3 | 5.13 | 4.7 | 18.5 | 23 | 1.6 | 0.2 | 1.2 | 1 | 0.3 |
| Patient 4 | 71 | M | PR | 10 | 15.13 | 7.2 | 63 | 36.5 | 2.5 | 0.5 | 4 | 2.2 | 0 |
| Patient 5 | 62 | M | CR | 6.3 | 5.13 | 2.5 | 14.4 | 53 | 0.5 | 3.0 | 4.5 | 2.4 | 1.17 |

METHOD FOR CANCER PROGNOSIS

CROSS REFERENCE TO RELATED APPLICATIONS

This application is the U.S. National Stage of International Application No. PCT/AU2018/050420, filed May 7, 2018, which claims the benefit of Australia Application No. AU 2017901660, filed May 5, 2017, the contents of which are hereby incorporated by reference in their entireties.

FIELD OF THE INVENTION

The present invention relates to methods of prognosing and monitoring cancer. In particular, the invention contemplates the use of circulating cells and/or extracellular vesicles as indicators of the progression of plasma cell neoplasms in patients. The invention further relates to determining the levels of extracellular vesicles including microparticles and exosomes comprising particular biomarker profiles in patients as indicators of the progression of plasma cell neoplasms.

BACKGROUND OF THE INVENTION

Any discussion of the prior art throughout the specification should in no way be considered as an admission that such prior art is widely known or forms part of common general knowledge in the field.

Survival rates from cancers are closely linked to the aggressiveness of the cancer, the presence of effective anti-cancer therapies and whether or not the cancer develops resistance to one or more anti-cancer therapies.

Some cancers become resistant to one or more anti-cancer therapies and this can happen rapidly, over days or weeks. Moreover, cancers can rapidly transition between active and inactive states, and progress. Many of the current methods of monitoring cancers are unable to determine if an inactive cancer has become active, or detect the resistance to an anti-cancer therapy(s), until the cancer has already become progressive or refractory to the therapy. Accordingly, it would be beneficial to be able to monitor the progression of a cancer as well as the emergence of resistance to anti-cancer therapies, such that treatment can be adapted before the cancer progresses significantly.

Common to many cancers is that methods of monitoring the progression of the cancers are invasive and cannot be performed as regularly as desired without patients being inconvenienced and subjected to painful tests. Moreover, the tests themselves may be onerous, expensive and time consuming. As such, the process of monitoring cancers as they transition between active and inactive states is often delayed, and this can be detrimental to the overall survival of patients as the administration of appropriate treatments is also delayed. For example, it would be of great benefit to be able to determine if a patient's cancer is transitioning from being remissive to progressive as soon as possible such that treatment can be modified.

Of even greater benefit would be the ability to make such a determination using a routine testing method that is quick, convenient and relatively painless for patients, while also not placing a large financial burden on both patients and the health care system. A flow on effect would be a greater willingness for patients to agree to such a test, thereby allowing closer monitoring of the cancer and better long-term outcomes.

Plasma cell neoplasms are a class of hematological diseases characterised by the overproduction of abnormal plasma cells, many of which are cancerous. One form of plasma cell neoplasm is myeloma, particularly multiple myeloma, and this occurs when abnormal plasma cells form tumours in the bone marrow interrupt the normal function of the plasma cells and bone marrow in general. Myeloma is the $14^{th}$ leading cause of cancer deaths in the United States.

According to the American Cancer Society, multiple myeloma has a 5-year survival rate of up to 50%, but this statistic may be misleading because patients with multiply myeloma have a high propensity for relapse. The high relapse rate in multiple myeloma is, in part, due to the high occurrence of resistance to anti-cancer therapies used to tread multiple myeloma patients.

Multiple myeloma is a complex disease that is often difficult to diagnose and monitor. Current methods for the diagnosis of multiple myeloma include physical examination, measuring $\beta$-2-microglobulin, albumin, monoclonal paraprotein (M-protein) in the blood and/or urine, bone-marrow biopsy optionally followed by cytogenic analysis, X-rays, MRI, CT-scan, complete blood counts and blood calcium level studies. Unfortunately, no single test is sufficient to accurately diagnose multiple myeloma and the tests chosen may depend on many factors such as perceived severity of the disease, age and health of the patient, financial considerations, availability of tests, and patient preference.

Newly diagnosed multiple myeloma patients are generally first treated with high dose combination chemotherapy and autologous stem cell transplantation. The necessary combination of anti-cancer therapies early in treatment can often lead to patients developing multi-drug resistance (MDR) cancer. MDR is a unique type of resistance in which cancer cells become cross-resistant to a broad range of drugs used in combination chemotherapy.

In general, the same tests used to diagnose multiple myeloma may be used to monitor the progression of multiple myeloma. As there are forms of myeloma that secrete little or no immunoglobulin and therefore can evade blood and urine tests, tests based on bone-marrow biopsy are arguably the most universally applicable and accurate for the diagnosis and monitoring of multiple myeloma. However, this procedure requires sedation or even anaesthesia, post-procedure pain relief medication, numerous trained medical practitioners to perform the biopsies at great expense, and also presents an additional infection risk to already immunocompromised patients.

Despite the usefulness of bone-marrow biopsies from a clinical perspective, even bone-marrow biopsies cannot directly and informatively assess the complexities associated with the staggered emergence of drug resistance. Moreover, as such biopsies cannot be performed every day, every week or even every month, it is not an appropriate method for determining or predicting the progression of the cancer in a timely and routine manner.

Additionally, other less invasive tests, such as those based on blood and urine samples, still only monitor tumour burden and are only useful when a disease has already re-emerged, as evidenced by a clinical manifestation. As such, they cannot provide a meaningly prognostic insight.

Specifically, there is a need for a method to accurately monitor plasma cell neoplasms using simple methods based on, preferably, peripheral blood samples, as opposed to relying heavily on bone marrow biopsy.

Extracellular vesicles, such as microparticles (also known as microvesicles or ectosomes), apoptotic bodies, oncosomes and exosomes, are released by a broad range of cells, including cancerous cells and cells that are precursors to cancer, as well as stem cells and progenitor cells. They are released into the extracellular environment, are capable of circulating and being transported throughout the body. Extracellular vesicles have been isolated from most biological fluids, such as saliva, blood, urine, ascites and cerebral fluid, mucus and breast milk. As extracellular vesicles often share characteristics with the cells from which they originate, they can be informative on the state of these cells. This is particularly advantageous for cells that are not ordinarily circulating, as the extracellular vesicles are easier to harvest.

One type of extracellular vesicle, microparticles, are small membrane vesicles (0.1 to 1 µm in diameter) released from the plasma membranes of most cell types and are present in peripheral blood, urine and other bodily fluids, such as saliva. As such, the microparticles will share some important characteristics of the plasma membranes of the cells from which they are derived, including, for example, the presence of particular membrane associated proteins.

Circulating cancer cell-derived extracellular vesicles have been detected in patients for a number of different cancers. It has been shown that some cancer cell-derived extracellular vesicles are involved in the transfer and spread of multidrug resistance within cancer cell populations and can do so in a matter of hours by carrying and transferring functional resistance proteins and nucleic acids.

In relation to multiple myeloma, the present inventors have previously reported the presence of extracellular vesicles that are positive for the marker protein CD138 (i.e., microparticles that are CD138$^+$) in the plasma of multiple myeloma patients, where it was observed that there were greater CD138$^+$ microparticle counts in multiple myeloma patients relative to healthy subjects (Krishnan, Bebawy et al., Neoplasia 2016; incorporated by reference). Interestingly, higher CD138$^+$ microparticle counts were detected for remissive patients (complete remission (CR), and partial remission (PR)) and patients with progressive disease (PD) relative to healthy subjects. However, no significant difference was observed between healthy subjects and newly diagnosed patients. In the reported study, 9 CR patients (defined using the International Myeloma Working Group (IMWG) response criteria) analysed had greater CD138$^+$ microparticle counts relative to the rest of the subjects. It was later found that 5 of those 9 CR patients relapsed clinically within 4 weeks of the study, demonstrating the potential for CD138$^+$ microparticle counts to predict the transition between inactive and active disease states before more conventional clinical markers.

However, of potentially greater use in a clinical setting would be a means of monitoring the progression of a myeloma, or even prognosing a myeloma in advance, with a minimally invasive test that can be performed routinely and easily. The ability to more closely monitor myeloma would allow for refinement of treatment strategies such as, for example, reducing medications once an improvement is detected, or modifying medications once a refractory cancer is detected or in advance of a predicted increase in severity of the cancer.

It is an object of the present invention to overcome or ameliorate at least one of the disadvantages of the prior art, or to provide a useful alternative.

SUMMARY OF THE INVENTION

It has been previously shown that circulating extracellular vesicles isolated from patients with multiple myeloma have distinct marker profiles that may be informative as to the prognosis of the patient. In particular, it was predicted that monitoring the level of extracellular vesicles that were positive for the marker protein CD138 (i.e., CD138$^+$ microparticles) could prove to be a useful prognostic tool for multiple myeloma.

Despite this earlier research, the present inventors have surprisingly found that the levels of extracellular vesicles that do not have the CD138 marker protein (CD138$^-$), but which are positive for at least P-glycoprotein (P-gp$^+$) in the plasma of patients with a plasma cell neoplasm is a superior indicator to disease progression.

Such a finding allows patients with a plasma cell neoplasm to be closely and accurately monitored serially by analysing cells originating from the bone marrow and/or extracellular vesicles, e.g., microvesicles derived from those cells in, for example, blood samples in the context of a 'liquid biopsy'. This reduces the reliance on invasive methods to monitor the cancers, such as bone-marrow biopsies. The cells, and extracellular vesicles that are derived from them, are essentially "surrogate markers" for difficult to access tissue in the bone marrow compartment.

The ability to continuously monitor patients for disease state phenotypes during the course of treatment allows for optimal patient management, as alternative therapies can be initiated promptly to prevent disease progression. This would be particularly useful in cases of non-secretory myeloma, which lack the classic manifestation of elevated M-protein levels and are consequently difficult to monitor.

Accordingly, in a first aspect of the present invention, there is provided a method for the prognosis of a patient with a plasma cell neoplasm or suspected of having a plasma cell neoplasm, comprising isolating a sample comprising extracellular vesicles from said patient and determining the level of extracellular vesicles that are CD138$^-$ and P-glycoprotein$^+$ (CD138$^-$/P-gp$^+$).

Advantageously, the method is an in vitro method that does not require painful or invasive techniques.

The method of the invention also does not necessarily require the isolation of neoplastic plasma cells from the bone marrow, and in preferred embodiments, the method only requires the isolation of circulating extracellular vesicles from biological fluids.

However, it would be understood that extracellular vesicles that are CD138$^-$ and P-gp$^+$ may be indicators of the presence of cells that do not have the CD138 marker protein, but which are positive for at least P-glycoprotein. The cells from which the extracellular vesicles are derived could be identified if the cells in the sample were subjected to the same or similar analytical techniques applied to determining the level of extracellular vesicles that are CD138$^-$ and P-gp$^+$. As these cells may also be circulating, they too can also be easy to isolate by non-invasive techniques.

Accordingly, in a second aspect of the present invention, there is provided a method for the prognosis of a patient with a plasma cell neoplasm or suspected of having a plasma cell neoplasm, comprising isolating a sample comprising cells from said patient and determining the level of cells that are CD138$^-$ and P-gp$^+$.

The patient may have, or be suspected of having, any plasma cell neoplasm. A plasma cell neoplasm is any disease which causes abnormal growth of plasma cells in the bone marrow. Plasma cell neoplasms include monoclonal gammopathy of undetermined significance (MGUS), plasmacytoma and multiple myeloma (including smoldering multiple myeloma and non-secretory myeloma). A myeloma may originate at one bone marrow site, but is almost always localised at more than bone marrow site in a patient, and is therefore commonly referred to as multiple myeloma.

The patient may have, or be suspected of having, a myeloma, or a multiple myeloma. In preferred embodiments of the invention, the patient has multiple myeloma.

In embodiments of the invention, there is provided method for the prognosis of a patient with multiple myeloma or suspected of having a multiple myeloma, comprising isolating a sample comprising extracellular vesicles from said patient and determining the level of extracellular vesicles that are $CD138^-$ and P-glycoprotein$^+$ ($CD138^-$/P-gp$^+$). In another embodiment, there is provided a method for the prognosis of a patient with multiple myeloma or suspected of having multiple myeloma, comprising isolating a sample comprising cells from said patient and determining the level of cells that are $CD138^-$/P-gp$^+$.

It would be understood that multiple myeloma is considered to be an incurable cancer and therefore a patient that has been diagnosed with multiple myeloma will always be deemed to have multiple myeloma irrespective of whether the patient enters remission and/or the cancer is no longer detectable. As such, the method of the invention may be used to periodically assess patients that have been deemed in remission or as having multiple myeloma that is no longer detectable to determine if the multiple myeloma may re-emerge clinically. The method of the invention may also be used to determine if a multiple myeloma has re-emerged, but is not yet detectable by conventional methods and/or does not yet have a clinical manifestation.

The multiple myeloma may have been initially diagnosed using any conventional disease indicators known in the art, including, but not limited to physical examination, measuring β-2-microglobulin, albumin, monoclonal paraprotein (M-protein) in the blood and/or urine, bone-marrow biopsy optionally followed by cytogenic analysis, X-rays, MRI, CT-scan, complete blood counts and blood calcium level studies.

The patient may have multiple myeloma at any stage, as classified by any classification method, including, but not limited to, the Durie-Salmon criteria or the International Staging System (ISS). The patient may be classified with a stage I, stage II or stage III myeloma.

It would be understood that a patient having a myeloma may be asymptomatic or symptomatic. For example, a patient diagnosed with an ISS stage II multiple myeloma may have a number of symptoms including, but not limited to, renal failure, frequent infection, bone pain, anaemia, lethargy in the limbs, breathing difficulties, nose bleeds and easy bruising as well as feelings of drowsiness, nausea and confusion. However, a patient having or suspected of having smoldering myeloma may have elevated M-protein levels, and elevated levels of plasma cells in the bone marrow, but this may not be accompanied by symptoms commonly associated with myeloma. In another example, a patient with MGUS may have elevated levels of M-protein but no other symptoms associated with myeloma.

Patients having a myeloma may experience fluctuations in the presence and emergence and severity of symptoms, and may fluctuate between being asymptomatic and symptomatic. It would also be understood that patients having or suspected of having MGUS or smoldering myeloma are likely to develop symptomatic myeloma during their lifetime.

In the context of the invention, a prognosis is a forecast as to the probable outcome of a plasma cell neoplasm (i.e., survival), or a forecast as to the next state a plasma cell neoplasm may proceed. The states of a plasma cell neoplasm are generally related to the rate at which neoplastic cells are proliferating, if the neoplasm is responding to treatment and/or the overall number of neoplastic cells that may be present in a patient. The states can also be defined in terms of whether the neoplasm is an active or inactive cancer, and can be relatively graded in terms of severity for a particular stage.

Using conventional methods, an evaluation of whether a myeloma is active or inactive would generally require that the myeloma be assessed on at least two consecutive time points to determine any change in disease indicators. In embodiments of the present invention, whether the myeloma is active or inactive may be determined at a single time point.

The present invention can also provide an early indication of whether a plasma cell neoplasm is likely to respond to treatment. In this capacity, the method of the invention may be considered a diagnostic method.

In the context of the present invention, a prognosis may also be a diagnosis of a particular state of the plasma cell neoplasm. The forecast as to the probable outcome of a plasma cell neoplasm may relate to the method of the invention providing an indication of the state of the plasma cell neoplasm at the time the method is performed on the patient. For example, the prognosis may be based on the method of the invention being performed on a patient suspected of having a plasma cell neoplasm, wherein it is determined the patient has a plasma cell neoplasm that is, or will likely become, refractory. In this instance, the diagnosis of this particular state is informative in a prognostic sense because it is indicative of a potentially poorer outcome for that patient when compared to a patient that is diagnosed as having a plasma cell neoplasm that is more likely going to be responsive to treatment.

In embodiments of the present invention, the method may be used to diagnose multiple myeloma. In this embodiment, the presence of cells and/or extracellular vesicles that are $CD138^-$/P-gp$^+$ in the patient may be indicative of the patient having an aggressive form of multiple myeloma.

Active myeloma states include responsive, stable, progressive and refractory, wherein a refractory myeloma is more severe than a progressive myeloma and a progressive myeloma is more severe than a stable myeloma and a stable myeloma is more severe than a responsive myeloma. Active myeloma states can occur at any stage of myeloma. For example, a patient may have a Stage II responsive myeloma (i.e. potentially moving towards being a Stage I myeloma) or a Stage I progressive myeloma (i.e., potentially moving towards a Stage II or Stage III myeloma).

A responsive myeloma is one where the myeloma is responding to one or more anti-cancer therapies, and may be characterised by the patient experiencing a reduction in the number and/or severity of symptoms over a period of time.

A stable myeloma is one where the myeloma is not getting worse, though the patient may still be symptomatic. A stable myeloma may be a responsive myeloma, such as, for example, in instances where a myeloma would be expected to increase in severity but remains stable in response to one or more anti-cancer therapies over a period of time.

A progressive myeloma is one where the myeloma is worsening, and may be characterised by the patient experiencing an increase in the number and severity of symptoms over a period of time.

A refractory myeloma is one that is not responsive to therapy, or not sufficiently responsive to therapy. A refractory myeloma may also be referred to as aggressive, resistant or non-responsive, and these terms are interchangeable.

Refractory myeloma may occur in patients who do not respond to one or more anti-cancer therapies or it may occur in patients who do initially respond to one or more anti-cancer therapies, but then become refractory to one or more anti-cancer therapies.

A myeloma at any stage may be refractory. It would be understood that a patient may develop a refractory myeloma that is not responsive to more than one anti-cancer therapy, which may be referred to as a multi-drug resistant (MDR) myeloma.

Inactive myeloma states include remissive states, such as partial remission and complete remission. A patient with smoldering myeloma or MGUS may be considered to have an inactive cancer.

A remissive myeloma is one where there is minimal or no evidence of the disease in the patient.

It would be understood that a sample used in the methods of the present invention may be any sample originating from a patient that would comprise cells, and therefore could also comprise extracellular vesicles such as, for example, a saliva sample, urine sample, breast milk sample, blood sample or a blood-derived sample.

The sample may comprise predominantly extracellular vesicles, or predominantly cells. In other embodiments, the sample may comprise a mixture of both cells and extracellular vesicles.

If the sample comprises both cells and extracellular vesicles, the method of the invention may only require that the level of the cells or the level of the extracellular vesicles be determined.

In some embodiments, the sample comprises both cells and extracellular vesicles, but only the level of cells that are CD138$^-$/P-gp$^+$ is determined when performing the method of the invention. In other embodiments, the sample comprises both cells and extracellular vesicles, but only the level of extracellular vesicles that are CD138$^-$/P-gp$^+$ is determined when performing the method of the invention.

In some embodiments, the sample comprises both cells and extracellular vesicles, and the level of cells that are CD138$^-$/P-gp$^+$, as well as the level of extracellular vesicles that are CD138$^-$/P-gp$^+$, is determined when performing the method of the invention.

In embodiments, the sample comprises both cells and extracellular vesicles, and the level of cells that are CD138$^-$/P-gp$^+$, as well as the level of extracellular vesicles that are CD138$^-$/P-gp$^+$, is determined when performing the method of the invention, and the method used to determine the level of cells that are CD138$^-$/P-gp$^+$ is different to the method used to determine the level of extracellular vesicles that are CD138$^-$/P-gp$^+$.

In alternative embodiments, the sample comprises both cells and extracellular vesicles, and the level of cells that are CD138$^-$/P-gp$^+$, as well as the level of extracellular vesicles that are CD138$^-$/P-gp$^+$, are determined when performing the method of the invention, and the method used to determine the level of cells that are CD138$^-$/P-gp$^+$ is the same as the method used to determine the level of extracellular vesicles that are CD138$^-$/P-gp$^+$.

Preferably, the sample is blood or a blood-derived sample. A blood-derived sample may be any sample wherein the starting material for preparing said sample is blood taken from the patient with a plasma cell neoplasm or suspected of having a plasma cell neoplasm. In more preferred embodiments of the invention, the sample is a plasma sample. The plasma may be obtained from any whole blood or serum sample collected from the patient, using methods known in the art.

In preferred embodiments of the invention, the plasma sample is platelet-free. Determining the level of extracellular vesicles or cells that are CD138$^-$/P-gp$^+$ in a plasma sample that is platelet free can minimise contamination by platelets and/or platelet-derived extracellular vesicles.

In other preferred embodiments of the invention, the extracellular vesicles or cells that are CD138$^-$/P-gp$^+$ are also CD41a$^-$. As CD41a is a typical platelet marker, this can minimise contamination by platelets and/or platelet-derived extracellular vesicles.

In embodiments of the invention, there is provided method for the prognosis of a patient with multiple myeloma or suspected of having a multiple myeloma, comprising isolating a sample comprising extracellular vesicles from said patient and determining the level of extracellular vesicles that are CD138$^-$/P-gp$^+$/CD41a$^-$. In another embodiment, there is provided a method for the prognosis of a patient with multiple myeloma or suspected of having multiple myeloma, comprising isolating a sample comprising cells from said patient and determining the level of cells that are CD138$^-$/P-gp$^+$/CD41a$^-$.

The sample may be an enriched or clarified sample predominantly comprising extracellular vesicles. By this is meant that steps may be taken to remove cells and other cellular and vesicular components and debris from the sample. Methods for preparing extracellular vesicles from blood-derived, urine or saliva samples are well known in the art and include, for example, centrifugation (i.e., density gradient centrifugation, differential centrifugation and ultra-centrifugation), immunoaffinity, filtration, sucrose gradients, electrophoresis, flow field-flow fractionation, and chromatographic techniques, such as size exclusion.

The sample may be an enriched or clarified sample predominantly comprising cells. By this is meant that steps may be taken to remove cellular debris and vesicular components from the sample. Methods for preparing cells from blood-derived, urine or saliva samples are well known in the art and include, for example, centrifugation, filtration, sucrose gradients, electrophoresis and chromatographic techniques.

In the present invention, the level of cells and/or extracellular vesicles that are CD138$^-$/P-gp$^+$ in the sample comprising cells and/or extracellular vesicles provides for the method of prognosis.

P-gp is a 170 kDa phosphoglycoprotein involved in multidrug efflux transport from the plasma membrane of cancer cells, and belongs to an ATP binding cassette superfamily. Other resistance markers that belong to the same family of proteins as P-gp include multidrug resistance protein 1 (MRP1, or ABCC1), ABCA1 and ABCG1. The skilled addressee would understand that these members of the same family are functionally redundant and can substitute in the absence of the other. Accordingly, for the purposes of the present invention, in the event P-gp is not detectable on the cells and/or extracellular vesicles present in a sample isolated from a patient with a plasma cell neoplasm or suspected of having a plasma cell neoplasm, the sample may be assayed for another member of the ATP binding cassette superfamily. CD138 is a transmembrane heparin sulphate proteoglycan and is expressed on the surface of normal mature plasma cells. Accordingly, normal mature plasma cells, and extracellular vesicles that are produced from normal mature plasma cells, will generally be CD138$^+$.

It has been surprisingly found that, in patients with a plasma cell neoplasm, the numbers of cells and/or extracellular vesicles that are positive for P-gp and negative for CD138 tend to increase as the disease progresses. In particular, it has been found that patients with an active form of multiple myeloma have higher levels of extracellular vesicles and/or cells that are CD138⁻/P-gp⁺ when compared to patients with inactive forms of multiple myeloma or healthy patients, thereby providing a useful prognostic and diagnostic indicator.

It has also been predicted in patients with a plasma cell neoplasm or patients suspected of having a plasma cell neoplasm, an elevated level of cells and/or extracellular vesicles that are CD138⁻/P-gp⁺ correlates with an increased likelihood that the patient has a plasma cell neoplasm that is, or will become, refractory.

In the context of the present invention, for an extracellular vesicle to be positive (+) for a particular target molecule, the molecule may be completely or partially contained within or located on the surface of the microparticle (i.e., a microparticle-associated protein or microparticle-associated phospholipid). The molecule may be full length protein or a fragment thereof, or a full length mRNA or fragment thereof that encodes the protein, and be in any orientation, and be detectable in the sample comprising the extracellular vesicles. The molecule may be detectable when the microparticle is intact or may only be detectable when the microparticle is ruptured. The molecule being detected may be any variant, isoform or polymorph of the target molecule.

In the context of the present invention, for a cell to be positive (+) for a particular target molecule, the molecule may be completely or partially contained within or located on the plasma membrane of the cell. The molecule may be full length protein or a fragment thereof, or a full length mRNA or fragment thereof that encodes the protein, and be in any orientation, and be detectable in the sample comprising the cells. The molecule may be detectable when the cell is intact or may only be detectable when the cell is rupture or lysed. The molecule being detected may be any variant, isoform or polymorph of the target molecule.

In the context of the present invention, for a cell or extracellular vesicle to be negative (−) for a particular target molecule, the molecule is not detectable on or within the cells and/or extracellular vesicles in the sample comprising the cells and/or extracellular vesicles. In the context of the present invention, when considering if a cell or extracellular vesicle is negative for a molecule, the molecule may be a full-length protein or fragment thereof.

For example, a sample may comprise cells that are determined to be P-gp⁺ and CD138⁻ because of the presence of P-gp protein and/or mRNA and the absence of CD138⁻ protein in a lysate of said cells. In a further example, a sample may comprise cells and extracellular vesicles that are determined to be P-gp⁺ and CD138⁻ because of the presence of P-gp epitopes and the absence of CD138⁻ epitopes on the surface of said cells and microparticles. In another example, a sample may comprise extracellular vesicles that are determined to be P-gp⁺ and CD138⁻ because of the presence of P-gp mRNA and the absence of the CD138⁻ protein or fragments thereof after said microvesicles are ruptured.

Accordingly, in embodiments of the invention, the level of extracellular vesicles being determined relates to a population of extracellular vesicles derived from the cells of a patient that comprise P-gp (P-gp⁺), but do not comprise CD138 (CD138⁻).

In other embodiments, the level of extracellular vesicles being determined relates to a population of extracellular vesicles derived from the cells of a patient that comprise P-gp (P-gp⁺), but do not comprise CD138 (CD138⁻) or CD41a (CD41a⁻).

In embodiments of the invention, the level of cells being determined relates to a population of cells that comprise P-gp (P-gp⁺), but do not comprise CD138 (CD138⁻).

In other embodiments, the level of cells being determined relates to a population of cells in a patient that comprise P-gp (P-gp⁺), but do not comprise CD138 (CD138⁻) or CD41a (CD41a⁻).

In embodiments of the method of prognosis of the invention, if the sample comprises cells and/or plasma-cell derived extracellular vesicles that are CD138⁻/P-gp⁺ at a level that is higher than a reference control indicative of a subject that does not have a plasma cell neoplasm or has a remissive plasma cell neoplasm, a prognosis that the neoplasm is stable, progressive or refractory is determined.

In other embodiments of the method of prognosis of the invention, if the sample comprises cells and/or extracellular vesicles that are CD138⁻/P-gp⁺ at a level that is higher than a reference control indicative of a subject with a stable plasma cell neoplasm, a prognosis that the neoplasm is progressive or refractory is determined.

In another embodiment of the method of prognosis of the invention, if the sample comprises cells and/or extracellular vesicles that are CD138⁻/P-gp⁺ at a level that is higher than a reference control indicative of a subject with a progressive plasma cell neoplasm, a prognosis that the neoplasm is refractory is determined.

The reference control indicative of a subject that does not have a plasma cell neoplasm may be from any non-cancer patient that has never been diagnosed with a plasma cell neoplasm with normal haematology.

The reference control indicative of a subject that has a remissive plasma cell neoplasm may be from any patient that has previously been diagnosed with a plasma cell neoplasm, but has not required treatment with anti-cancer therapies for a period of at least 6 months and whose M-protein levels undetectable in the blood, urine and/or saliva.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is higher than a reference control indicative of a subject that does not have multiple myeloma or has a remissive multiple myeloma, a prognosis that the multiple myeloma is stable, progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is higher than a reference control indicative of a subject with stable multiple myeloma, a prognosis that the multiple myeloma is progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is higher than a reference control indicative of a subject with progressive multiple myeloma, a prognosis that the multiple myeloma is refractory is determined.

For the purposes of the methods of the invention, whether or not the level of cells and/or extracellular vesicles that are CD138⁻/P-gp⁺ in the sample is higher than the reference control may be determined by a direct comparison or by a comparison to a pre-determined level indicative of a subject that does not have a plasma cell neoplasm or has a remissive, stable or progressive plasma cell neoplasm. The level of the cells or the extracellular vesicles may be determined qualitatively or quantitatively, and may relate to an absolute number of cells and/or extracellular vesicles that are CD138⁻/P-gp⁺ in a particular sample, or may relate to a concentration of cells and/or extracellular vesicles that are CD138⁻/P-gp⁺ in a particular sample, or may relate to a visual determination of the presence or absence of cells and/or extracellular vesicles that are CD138⁻/P-gp⁺ in a particular sample.

The level may be determined in a sample, and then correlated to an absolute number in the patient or a concentration in, for example, the blood, urine or saliva of the patient. The level of the cells and/or extracellular vesicles that are CD138⁻/P-gp⁺ in a particular sample need not be determined in the same way as the level of the of cells and/or extracellular vesicles that are CD138⁻/P-gp⁺ are determined in the reference control, provided there is a means of comparing the levels.

In embodiments of the present invention, for the level of the cells and/or extracellular vesicles that are CD138⁻/P-gp⁺ in the sample to be higher than a reference control, the level of vesicles and/or extracellular vesicles is at least 1.01 times higher than the level of the cells and/or extracellular vesicles that are CD138–/P-gp+ in the reference control. For example, the level of vesicles and/or extracellular vesicles in the sample that are CD138⁻/P-gp⁺/CD34⁺ may be at least 1.01, 1.1, 1.5, 2, 3, 4, 5, 10, 25, 50, 100 or 1000 times higher than the level of the cells and/or extracellular vesicles that are CD138⁻/P-gp⁺/CD34⁺ in the reference control. In another example, the level of vesicles and/or extracellular vesicles in the sample that are CD138⁻/P-gp⁺/CD34⁺/CD41a⁻ may be at least 1.01, 1.1, 1.5, 2, 3, 4, 5, 10, 25, 50, 100 or 1000 times higher than the level of the cells and/or extracellular vesicles that are CD138⁻/P-gp⁺/CD34⁺/CD41a⁻ in the reference control. In further examples, the level of vesicles and/or extracellular vesicles in the sample that are CD138⁻/P-gp⁺/CD41a⁻ may be at least 1.01, 1.1, 1.5, 2, 3, 4, 5, 10, 25, 50, 100 or 1000 times higher than the level of the cells and/or extracellular vesicles that are CD138⁻/P-gp⁺/CD41a⁻ in the reference control.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is at least 1.1 times higher than a reference control indicative of a subject that does not have multiple myeloma or has a remissive multiple myeloma, a prognosis that the multiple myeloma is stable, progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is at least 1.1 times higher than a reference control indicative of a subject with stable multiple myeloma, a prognosis that the multiple myeloma is progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is at least 1.1 times higher than a reference control indicative of a subject with progressive multiple myeloma, a prognosis that the multiple myeloma is refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is at least 2 times higher than a reference control indicative of a subject that does not have multiple myeloma or has a remissive multiple myeloma, a prognosis that the multiple myeloma is stable, progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is at least 2 times higher than a reference control indicative of a subject with stable multiple myeloma, a prognosis that the multiple myeloma is progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is at least 2 times higher than a reference control indicative of a subject with progressive multiple myeloma, a prognosis that the multiple myeloma is refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138⁻/P-gp⁺, wherein when the sample comprises cells and/or extracellular vesicles that are CD138⁻/P-gp⁺ at a level that is at least 5 times higher than a reference control indicative of a subject that does not have multiple myeloma or has a remissive multiple myeloma, a prognosis that the multiple myeloma is stable, progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138$^-$/P-gp$^+$, wherein when the sample comprises cells and/or extracellular vesicles that are CD138$^-$/P-gp$^+$ at a level that is at least 5 times higher than a reference control indicative of a subject with stable multiple myeloma, a prognosis that the multiple myeloma is progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138$^-$/P-gp$^+$, wherein when the sample comprises cells and/or extracellular vesicles that are CD138$^-$/P-gp$^+$ at a level that is at least 5 times higher than a reference control indicative of a subject with progressive multiple myeloma, a prognosis that the multiple myeloma is refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138$^-$/P-gp$^+$/CD34$^+$, wherein when the sample comprises cells and/or extracellular vesicles that are CD138$^-$/P-gp$^+$/CD34$^+$ at a level that is at least 1.1 times higher than a reference control indicative of a subject that does not have multiple myeloma or has a remissive multiple myeloma, a prognosis that the multiple myeloma is stable, progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138$^-$/P-gp$^+$/CD34$^+$, wherein when the sample comprises cells and/or extracellular vesicles that are CD138$^-$/P-gp$^+$/CD34$^+$ at a level that is at least 1.1 times higher than a reference control indicative of a subject with stable multiple myeloma, a prognosis that the multiple myeloma is progressive or refractory is determined.

In embodiments of the invention, there is provided method for the prognosis of a patient with multiple myeloma or suspected of having a multiple myeloma, comprising isolating a sample comprising cells and/or extracellular vesicles from said patient and determining the level of cells and/or extracellular vesicles that are CD138$^-$/P-gp$^+$/CD34$^+$, wherein when the sample comprises cells and/or extracellular vesicles that are CD138$^-$/P-gp$^+$/CD34$^+$ at a level that is at least 1.1 times higher than a reference control indicative of a subject with progressive multiple myeloma, a prognosis that the multiple myeloma is refractory is determined.

The populations of cells and/or extracellular vesicles described above can also be exploited to monitor the progress of a plasma cell neoplasm over time in a particular patient, as increasing levels of cells and/or extracellular vesicles that are CD138$^-$/P-gp$^+$ in a patient with a myeloma have been shown to be indicative of an increase in the severity of the myeloma.

Accordingly, in third aspect of the present invention, there is provided a method for monitoring the progression of a patient with a plasma cell neoplasm or suspected of having a plasma cell neoplasm, comprising isolating a sample comprising cells and/or extracellular vesicles from said patient at least two time points and determining the change in the level of cells and/or extracellular vesicles that are CD138$^-$/P-gp$^+$.

The change in level of cells and/or extracellular vesicles that are CD138$^-$/P-gp$^+$ may be an absolute value or may be relative to other populations of cells and/or extracellular vesicles, respectively.

The time points may be separated by any period of time, from days to years. The change in level of relevant extracellular vesicles may be determined across two time points, and may be continuously determined over multiple time points. For example, the level of cells and/or extracellular vesicles that are CD138$^-$/P-gp$^+$ may be determined at a first, second, third and fourth time-point, wherein each time point is separated by 1 week. The change in level of cells and/or extracellular vesicles that are CD138$^-$/P-gp$^+$ may be determined by comparing the first and second time point, the second and fourth time point or the first and third time point.

The time points may be separated by the same of different periods of time. For example, a first and second time point may be two weeks apart, while a third time point may be 6 months after the second time point.

In embodiments of the invention, an increase in the level of cells and/or extracellular vesicles that are CD138$^-$/P-gp$^+$ between subsequent time points may provide a diagnosis of a plasma cell neoplasm. For example, at a first time point, a patient may not have a detectable level of cells and/or extracellular vesicles that are CD138$^-$/P-gp$^+$, but then may have a detectable level of cells and/or extracellular vesicles that are CD138$^-$/P-gp$^+$ at a second time point, which may be indicative of a plasma cell neoplasm that has emerged, or may emerge.

In embodiments of the invention, an increase in the level of cells and/or extracellular vesicles that are CD138$^-$/P-gp$^+$ between subsequent time points may provide a diagnosis of a refractory plasma cell neoplasm. For example, at a first time point, a patient may not have a detectable level of cells and/or extracellular vesicles that are CD138$^-$/P-gp$^+$, but then may have a detectable level of cells and/or extracellular vesicles that are CD138$^-$/P-gp$^+$ at a second time point, which may be indicative of a plasma cell neoplasm that has become refractory.

In embodiments of the invention, an increase in the level of cells and/or extracellular vesicles that are CD138$^-$/P-gp$^+$ between subsequent time points is indicative that the severity of the plasma cell neoplasm is increasing.

In embodiments of the present invention, for the level of the cells and/or extracellular vesicles that are CD138$^-$/P-gp$^+$ to increase over time, the level of vesicles and/or extracellular vesicles that are CD138$^-$/P-gp$^+$ in a sample at one time point is at least 1.01 times higher than the level of the cells and/or extracellular vesicles that are CD138$^-$/P-gp$^+$ in a sample from an earlier time point. For example, the level of vesicles and/or extracellular vesicles in a sample at one time point that are CD138$^-$/P-gp$^+$ may be at least 1.01, 1.1, 1.5, 2, 3, 4, 5, 10, 25, 50, 100 or 1000 times higher than the level of the cells and/or extracellular vesicles in a sample from an earlier time point that are CD138$^-$/P-gp$^+$. In another example, the level of vesicles and/or extracellular vesicles in a sample at one time point that are CD138$^-$/P-gp$^+$/CD34$^+$ may be at least 1.01, 1.1, 1.5, 2, 3, 4, 5, 10, 25, 50, 100 or 1000 times higher than the level of the cells and/or extracellular vesicles in a sample from an earlier time point that are CD138$^-$/P-gp$^+$/CD34$^+$. In further examples, the level of vesicles and/or extracellular vesicles in a sample at one time point that are CD138$^-$/P-gp$^+$/CD34$^+$/CD41a$^-$ may be at least 1.01, 1.1, 1.5, 2, 3, 4, 5, 10, 25, 50, 100 or 1000 times higher than the level of the cells and/or extracellular vesicles in a sample from an earlier time point that are CD138$^-$/P-gp$^+$/CD34$^+$/CD41a$^-$.

By increasing in severity is meant that the neoplasm is shifting, or has shifted, from an inactive to active state, or is shifting, or has shifted, from one active state to a more severe active state. For example, in a patient that is determined to have a remissive myeloma based on M-protein levels, an increase in the level of cells and/or extracellular vesicles that are CD138$^-$/P-gp$^+$ between subsequent time points may be indicative that the myeloma is shifting, or has shifted, to a stable myeloma. In this instance, the early prognosis provided by the method of the present invention could allow for treatment to be commenced before the myeloma becomes active again.

In another example, in a patient with a myeloma that appears to be responsive, an increase in the level of cells and/or extracellular vesicles that are CD138$^-$/P-gp$^+$ between subsequent time points may be indicative that the myeloma is shifting, or has shifted, to a progressive myeloma. In this instance, the early prognosis provided by the method of the invention could allow for the treatment regimes to be modified.

In another embodiment, in a patient with a progressive myeloma that is being treated by numerous anti-cancer therapies, the level of cells and/or extracellular vesicles that are CD138$^-$/P-gp$^+$ at subsequent time points may be monitored for the emergence of a refractory myeloma. In this instance, the time points may be separated by days, weeks or months such that the responsiveness of the myeloma to the therapies may be closely monitored and changed if need be.

In embodiments of the invention, there is provided a method for monitoring the progression of a patient with a plasma cell neoplasm or suspected of having a plasma cell neoplasm, comprising isolating a sample comprising cells and/or extracellular vesicles from said patient at at least two time points and determining the change in the level of cells and/or extracellular vesicles that are CD138$^-$/P-gp$^+$/CD34$^+$/PS$^+$/CD41a$^-$, wherein an increase in the level of cells and/or extracellular vesicles that are CD138$^-$/P-gp$^+$/CD34$^+$/PS$^+$/CD41a$^-$ between subsequent time points of at least 1.1 is indicative that the severity of the plasma cell neoplasm is increasing.

In further embodiments, there is provided a method for monitoring the progression of a patient with multiple myeloma or suspected of having multiple myeloma, comprising isolating a sample comprising cells and/or extracellular vesicles from said patient at at least two time points and determining the change in the level of cells and/or extracellular vesicles that are CD138$^-$/P-gp$^+$/CD34$^+$, wherein an increase in the level of cells and/or extracellular vesicles that are CD138$^-$/P-gp$^+$/CD34$^+$ between subsequent time points of at least 1.1 is indicative that the severity of the plasma cell neoplasm is increasing.

In another embodiment, there is provided a method for monitoring the progression of a patient with multiple myeloma or suspected of having multiple myeloma, comprising isolating a blood-derived sample comprising cells and/or extracellular vesicles from said patient at least two time points at least 2 weeks apart and determining the change in the level of cells and/or extracellular vesicles that are CD138$^-$/P-gp$^+$/CD41a$^-$, wherein an increase in the level of cells and/or extracellular vesicles that are CD138$^-$/P-gp$^+$/CD41a$^-$ between subsequent time points of at least 1.1 is indicative that the severity of the plasma cell neoplasm is increasing.

In embodiments of the invention, a decrease in the level of cells and/or extracellular vesicles that are CD138$^-$/P-gp$^+$ between subsequent time points is indicative that the severity of the plasma cell neoplasm is decreasing.

In embodiments of the present invention, for the level of the cells and/or extracellular vesicles that are CD138$^-$/P-gp$^+$ to decrease over time, the level of vesicles and/or extracellular vesicles that are CD138$^-$/P-gp$^+$ in a sample at one time point are at least 0.99 times smaller than the level of the cells and/or extracellular vesicles that are CD138$^-$/P-gp$^+$ in a sample from an earlier time point. For example, the level of vesicles and/or extracellular vesicles in a sample at one time point that are CD138$^-$/P-gp$^+$ may be at least 0.99, 0.90, 0.66, 0.5, 0.4, 0.3, 0.2, 0.1, 0.04, 0.02, 0.01, 0.001 times smaller than the level of the cells and/or extracellular vesicles in a sample from an earlier time point that are CD138$^-$/P-gp$^+$. In another example, the level of vesicles and/or extracellular vesicles in a sample at one time point that are CD138$^-$/P-gp$^+$/CD34$^+$ may be at least 0.99, 0.90, 0.66, 0.5, 0.4, 0.3, 0.2, 0.1, 0.04, 0.02, 0.01, 0.001 times smaller than the level of the cells and/or extracellular vesicles in a sample from an earlier time point that are CD138$^-$/P-gp$^+$/CD34$^+$. In further examples, the level of vesicles and/or extracellular vesicles in a sample at one time point that are CD138$^-$/P-gp$^+$/CD34$^+$/CD41a$^-$ may be at least 0.99, 0.90, 0.66, 0.5, 0.4, 0.3, 0.2, 0.1, 0.04, 0.02, 0.01, 0.001 times smaller than the level of the cells and/or extracellular vesicles in a sample from an earlier time point that are CD138$^-$/P-gp$^+$/CD34$^+$/CD41a$^-$.

By decreasing in severity is meant that the neoplasm is shifting, or has shifted, from an active to inactive state, or is shifting, or has shifted, from one active state to a less severe active state or is responding, or is becoming responsive, to treatment.

In embodiments of the invention, there is provided a method for monitoring the progression of a patient with a plasma cell neoplasm or suspected of having a plasma cell neoplasm, comprising isolating a sample comprising cells and/or extracellular vesicles from said patient at at least two time points and determining the change in the level of cells and/or extracellular vesicles that are CD138$^-$/P-gp$^+$/CD34$^+$/PS$^+$/CD41a$^-$, wherein a decrease in the level of cells and/or extracellular vesicles that are CD138$^-$/P-gp$^+$/CD34$^+$/PS$^+$/CD41a$^-$ between subsequent time points of at least 0.9 is indicative that the severity of the plasma cell neoplasm is decreasing.

In further embodiments, there is provided a method for monitoring the progression of a patient with multiple myeloma or suspected of having multiple myeloma, comprising isolating a sample comprising cells and/or extracellular vesicles from said patient at at least two time points and determining the change in the level of cells and/or extracellular vesicles that are CD138$^-$/P-gp$^+$/CD34$^+$, wherein a decrease in the level of cells and/or extracellular vesicles that are CD138$^-$/P-gp$^+$/CD34$^+$ between subsequent time points of at least 0.9 is indicative that the severity of the plasma cell neoplasm is decreasing.

In another embodiment, there is provided a method for monitoring the progression of a patient with multiple myeloma or suspected of having multiple myeloma, comprising isolating a blood-derived sample comprising cells and/or extracellular vesicles from said patient at at least two time points at least 2 weeks apart and determining the change in the level of cells and/or extracellular vesicles that are CD138$^-$/P-gp$^+$/CD41a$^-$, wherein a decrease in the level of cells and/or extracellular vesicles that are CD138$^-$/P-gp$^+$/

CD41a⁻ between subsequent time points of at least 0.9 is indicative that the severity of the plasma cell neoplasm is decreasing.

The present inventors have also found determining the level of cells and/or extracellular vesicles that are $CD138^-/P\text{-}gp^+$, as well as being $CD34^+$, provides a more sensitive indication of the prognosis of a plasma cell neoplasm. CD34 is a transmembrane protein that is found on haematopoietic stem cells and used as a stem cell marker.

Accordingly, in preferred embodiments of the methods of the invention, the level of cells and/or extracellular vesicles being determined relates to a population of cells and/or extracellular vesicles that are $CD138^-/P\text{-}gp^+/CD34^+$.

In other preferred embodiments of the methods of the invention, the level of cells and/or extracellular vesicles being determined relates to a population of cells and/or extracellular vesicles that are $CD138^-/P\text{-}gp^+/CD34^+/CD41a^-$.

In embodiments of the invention, there is provided method for the prognosis of a patient with multiple myeloma or suspected of having a multiple myeloma, comprising isolating a blood-derived sample comprising extracellular vesicles from said patient and determining the level of extracellular vesicles that are $CD138^-/P\text{-}gp^+/CD34^+/CD41a^-$. In another embodiment, there is provided a method for the prognosis of a patient with multiple myeloma or suspected of having multiple myeloma, comprising isolating a blood-derived sample comprising cells from said patient and determining the level of cells that are $CD138^-/P\text{-}gp^+/CD34^+/CD41a^-$.

The present inventors have also found determining the level of cells and/or extracellular vesicles that are $CD138^-/P\text{-}gp^+$, as well as being positive for phosphatidylserine ($PS^+$), provides a more sensitive indication of the prognosis of a plasma cell neoplasm. PS is a phospholipid commonly associated with plasma cell membranes.

In preferred embodiments of the methods of the invention, the level of cells and/or extracellular vesicles being determined relates to a population of cells and/or extracellular vesicles that are $CD138^-/P\text{-}gp^+/CD34^+/PS^+$.

In particularly preferred embodiments of the methods of the invention, the level of cells and/or extracellular vesicles being determined relates to a population of cells and/or extracellular vesicles that are $CD138^-/P\text{-}gp^+/CD34^+/PS^+/CD41a^-$.

In embodiments of the invention, there is provided method for the prognosis of a patient with multiple myeloma or suspected of having a multiple myeloma, comprising isolating a blood-derived sample comprising extracellular vesicles from said patient and determining the level of extracellular vesicles that are $CD138^-/P\text{-}gp^+/CD34^+/PS^+/CD41a^-$. In another embodiment, there is provided a method for the prognosis of a patient with multiple myeloma or suspected of having multiple myeloma, comprising isolating a blood-derived sample comprising cells from said patient and determining the level of cells that are $CD138^-/P\text{-}gp^+/CD34^+/PS^+/CD41a^-$.

In further embodiments, there is provided a method for monitoring the progression of a patient with a plasma cell neoplasm or suspected of having a plasma cell neoplasm, comprising isolating a sample comprising cells and/or extracellular vesicles from said patient at at least two time points and determining the change in the level of cells and/or extracellular vesicles that are $CD138^-/P\text{-}gp^+/CD34^+/PS^+/CD41a^-$.

It would be understood that the cells that are overproduced and/or become abnormal and/or are $CD138^-/P\text{-}gp^+$ in a patient with a plasma cell neoplasm would be produced or have their origins in the bone marrow. At any stage of development, cells may migrate out of the bone marrow such that they become circulating cells that may be present in a sample used in the methods of the present invention.

The bone marrow contains blood cells at varying stages of development. However, the characterisation of cells that are $CD138^-/P\text{-}gp^+$, and the cells from which they may originate, is problematic because the cells may, for example, become de-differentiated and/or shed "known" cell surface markers used for conventional identification methods and/or divide and never fully differentiate into a cell type that can be characterised by conventional methods. These factors also make it difficult to characterise the developmental stage of the cells.

Moreover, while cells that become neoplastic when a patient has a plasma cell neoplasm are often referred to as "plasma cells", this may actually reflect a heterogeneous population of many different plasma-like cells or cells that developmentally precede plasma cells. Without wishing to be limited by theory, it is proposed that precursor cells that may not be deemed as neoplastic or plasma cells can also be informative for the prognosis and diagnosis of plasma cell neoplasms.

As such, the sample used in the methods of the invention may contain any cells that are produced in the bone marrow, which may include, for example, cells that originate from hematopoietic stem cells or mesenchymal stem cells. The hematopoietic stem cells can generally be identified by the presence of the hematopoietic stem cell marker, CD34, while the mesenchymal stem cells generally do not express CD34 on their cell surface.

In embodiments of the present invention, the sample comprises cells that are hematopoietic stem cells or originated from hematopoietic stem cells. The cells in the sample may be classified as hematopoietic stem cells, or the cells may have differentiated beyond the stem cell stage. This differentiation of the hematopoietic stem cells to become the cells in the sample used for the method of the invention may have been typical or abnormal.

Typically, one of the earlier stages of hematopoietic stem cell differentiation is the differentiation into either myeloid progenitor cells or lymphoid progenitor cells. The myeloid progenitor cells eventually develop into numerous different cell types including the red blood cells, platelets, granulocytes and macrophages.

Accordingly, in embodiments of the invention, the sample comprises cells that are myeloid progenitor cells or originated from myeloid progenitor cells. In other embodiments of the invention, the sample comprises cells that are lymphoid progenitor cells or originated from lymphoid progenitor cells.

Typically, the lymphoid progenitor cells undergo further development into T lymphocyte cells, Natural killer cells and B lymphocyte cells. The B lymphocytes, upon activation, become plasma cells that produce antibodies. In general, the B cells are associated with plasma cell neoplasms because the neoplasms are believed to start with the production of one of more abnormal plasma cells (or "plasma-like" cells) that do not subsequently undergo cell death, but rather, continue to divide in an unregulated manner. The plasma-like cells may be phenotypically similar to plasma cells that have developed typically or may differ in, for example, size, morphology cell-surface markers, migratory pattern and/or cell-cycle length Accordingly, in embodiments of the invention, the sample comprises cells that originated from B lymphocyte cells.

At any stage of development, any of the above mentioned cells may become circulating cells that may be present in a sample used in the methods of the present invention.

The sample used in the method of the invention may be an enriched or clarified sample predominantly comprising a particular cell type. By this is meant that steps may be taken to remove unwanted cell types from the sample, and this may be achieved by, for example, centrifugation methods, affinity methods based on particular cell-surface markers, or by exploiting size, density or morphological differences. For example, lymphoid progenitor cells and cells originating from lymphoid progenitor cells may comprise the cell surface marker, CD34 and/or CD38 and/or Neprilysin, and this may be used to isolate these cells by immunoaffinity methods.

The samples used in the methods of the present invention may contain extracellular vesicles produced or derived from any of the cells described above. Any individual cell or particular cell type can release more than one type of extracellular vesicle.

The sample may contain extracellular vesicles produced from cells that are not circulating or cells that remain in, or form part, of various tissues. For example, the sample may comprise extracellular vesicles from cells in the bone marrow, or the endothelium or the thymus that have entered the bloodstream of the patient. For patients with a plasma cell neoplasm, the sample may comprise extracellular vesicles that have been shed from neoplastic plasma cells in various tissues before entering the blood, saliva or urine of the patient, or shed from neoplastic plasma cells that are already present in the blood, saliva or urine of the patient.

The extracellular vesicles may have been produced by abnormal plasma cells or plasma-like cells, such as those produced by a patient with a myeloma.

The sample may comprise other cell types and/or cellular components and/or vesicular components provided these components do not appreciably interfere with the assays for determining the levels of said plasma cells and/or plasma cell-derived extracellular vesicles.

The extracellular vesicles comprised in the samples used in the methods of the present invention may be any vesicle comprising a phospholipid membrane bilayer released into the intercellular environment. The vesicles may be generally spherical and range in size from 1 nm to 10000 nm across, and may comprise proteins, RNA, DNA and lipids from the cells from which they are derived. In general, the composition of the extracellular vesicle reflects that of the cell from which it was derived.

The extracellular vesicles include, for example, exosomes, microparticles, oncosomes, large oncosomes, migrasomes and apoptotic vesicles. Exosomes have endosomal origins and are released from cells by the fusion of multivesicular endosomes with the cell's plasma membrane. Microparticles bud directly from the cell's plasma membrane, and their membrane composition is often closely related to their parent cells. Apoptotic bodies are larger extracellular vesicles released by cells as the plasma membrane fragments during apoptosis, and may comprise additional components such as organelles and nuclear fragments.

In general, any extracellular vesicle comprising structurally and functionally abnormal, mutant and potentially transforming molecules (i.e., oncogenes and/or oncoproteins etc), which are released from tumour cells, may be referred to as oncosomes. Large oncosomes are a distinct category of oncosomes that are derived from aggressive or metastatic tumour cells, via budding or blebbing of the plasma membrane, and contain oncogenic material. Migrasomes are extracellular vesicles derived from the rear edge (trailing edge) of migrating cells that allow communication between migrating cells, and may contain smaller internal vesicles.

It would be understood that a particular extracellular vesicle in a sample used in the methods of the present invention may be capable of being categorised as more than one different type of extracellular vesicle. For example, an exosome released from an abnormal plasma cell in a patient with a plasma cell neoplasm may also be referred to as an oncosome.

The samples used in the methods of the present invention may comprise a mixture of exosomes, microparticles, oncosomes, large oncosomes, migrasomes, apoptotic vesicles and/or any other extracellular vesicle. Preferably, the sample comprises exosomes and/or microparticles.

In embodiments of the invention, the extracellular vesicles are microparticles, which are often referred to as microvesicles or ectosomes.

The microparticles used in the methods of the present invention are small membrane vesicles that are generated by the budding of plasma membranes of most cell types. The sample may comprise a heterogeneous population of microparticles. The size of the microparticles may be typically, but not limited to, 0.1-1 mm in diameter.

In embodiments of the invention, there is provided method for the prognosis of a patient with multiple myeloma or suspected of having a multiple myeloma, comprising isolating a sample comprising cells produced in the bone marrow and/or or microparticles derived from cells produced in the bone marrow from said patient and determining the level cells produced in the bone marrow and/or or microparticles derived from cells produced in the bone marrow that are $CD138^-/P\text{-}gp^+/CD41a^-$, wherein when the sample comprises cells produced in the bone marrow and/or or microparticles derived from cells produced in the bone marrow that are $CD138^-/P\text{-}gp^+/CD41a^-$ at a level that is at least 1.1 times higher than a reference control indicative of a subject that does not have multiple myeloma or has a remissive multiple myeloma, a prognosis that the multiple myeloma is stable, progressive or refractory is determined.

In embodiments of the invention, there is provided method for the prognosis of a patient with multiple myeloma or suspected of having a multiple myeloma, comprising isolating a sample comprising cells produced in the bone marrow and/or or microparticles derived from cells produced in the bone marrow from said patient and determining the level of cells produced in the bone marrow and/or or microparticles derived from cells produced in the bone marrow that are $CD138^-/P\text{-}gp^+/CD41a^-$, wherein when the sample comprises cells produced in the bone marrow and/or or microparticles derived from cells produced in the bone marrow that are $CD138^-/P\text{-}gp^+/CD41a^-$ at a level that is at least 1.1 times higher than a reference control indicative of a subject with stable multiple myeloma, a prognosis that the multiple myeloma is progressive or refractory is determined.

In embodiments of the invention, there is provided method for the prognosis of a patient with multiple myeloma or suspected of having a multiple myeloma, comprising isolating a sample comprising cells produced in the bone marrow and/or or microparticles derived from cells produced in the bone marrow from said patient and determining the level of cells produced in the bone marrow and/or or microparticles derived from cells produced in the bone marrow that are $CD138^-/P\text{-}gp^+/CD41a^-$, wherein when the sample comprises cells produced in the bone marrow and/or or microparticles derived from cells produced in the bone marrow that are $CD138^-/P\text{-}gp^+/CD41a^-$ at a level that is at least 1.1 times higher than a reference control indicative of a subject with progressive multiple myeloma, a prognosis that the multiple myeloma is refractory is determined.

In another embodiment, there is provided a method for monitoring the progression of a patient with multiple myeloma or suspected of having multiple myeloma, comprising isolating a blood-derived sample comprising cells produced in the bone marrow and/or or microparticles derived from cells produced in the bone marrow from said patient at least two time points at least 2 weeks apart and determining the change in the level of cells produced in the bone marrow and/or or microparticles derived from cells produced in the bone marrow that are $CD138^-/P\text{-}gp^+/CD41a^-$, wherein an increase in the level of cells produced in the bone marrow and/or or microparticles derived from cells produced in the bone marrow that are $CD138^-/P\text{-}gp^+/CD41a^-$ between subsequent time points of at least 1.1 times is indicative that the severity of the plasma cell neoplasm is increasing.

In another embodiment, there is provided a method for monitoring the progression of a patient with multiple myeloma or suspected of having multiple myeloma, comprising isolating a blood-derived sample comprising cells produced in the bone marrow and/or or microparticles derived from cells produced in the bone marrow from said patient at at least two time points at least 2 weeks apart and determining the change in the level of cells produced in the bone marrow and/or or microparticles derived from cells produced in the bone marrow that are $CD138^-/P\text{-}gp^+/CD41a^-$, wherein a decrease in the level of cells produced in the bone marrow and/or or microparticles derived from cells produced in the bone marrow that are $CD138^-/P\text{-}gp^+/CD41a^-$ between subsequent time points of at least 0.9 is indicative that the severity of the plasma cell neoplasm is decreasing.

In embodiments of the invention, the extracellular vesicles are exosomes. The sample may comprise a heterogeneous population of exosomes with sizes ranging from 1-200 nm in diameter.

In embodiments of the invention, the extracellular vesicles are apoptotic vesicles. The sample may comprise a heterogeneous population of apoptotic vesicles with sizes ranging from 1000-5000 nm in diameter.

In embodiments of the invention, the extracellular vesicles are large oncosomes. The sample may comprise a heterogeneous population of large oncosomes with sizes ranging from 1000-10000 nm in diameter.

In embodiments of the invention, the extracellular vesicles are migrasomes. The sample may comprise a heterogeneous population of migrasomes with sizes ranging from 500-1500 nm in diameter.

The sample used in the method of the invention may be an enriched or clarified sample predominantly comprising exosomes, microparticles, oncosomes, large oncosomes, migrasomes and apoptotic vesicles. By this is meant that steps may be taken to remove unwanted extracellular vesicles from the sample, and this is generally done by exploiting the size and density differences between the types of extracellular vesicles, which may be confirmed by microscopic analysis. Samples comprising predominantly exosomes, microparticles, oncosomes, large oncosomes, migrasomes and apoptotic vesicles may be prepared via, for example, differential centrifugation, size-exclusion chromatography, polymeric precipitation methods, aqueous two phase systems, sucrose gradient centrifugation and microfiltration.

Populations of extracellular vesicles predominantly comprising exosomes, microparticles, oncosomes, large oncosomes, migrasomes or apoptotic vesicles may be isolated by via methods involving differential centrifugation.

For example, exosomes may be isolated by ultracentrifugation at 100,000-200,000 g, while microparticles may be isolated by centrifugation at 10,000-20,000 g. Microparticles may be isolated using higher speed centrifugation, but these samples may also include some exosomes.

Populations of extracellular vesicles predominantly comprising exosomes, microparticles, oncosomes, large oncosomes, migrasomes or apoptotic vesicles may also be isolated by affinity methods that rely on particular markers. For example, exosomes may be isolated via the presence of tetraspanins, components of the endosomal sorting complex required for transport (ESCRT) such as Alix, ceramide, flotillin, Rab and TSG101, as well as other proteins involved in exosomes biogenesis. Microparticles may be isolated via the presence of integrins, selectins and membrane related markers from their parent cells, as well as ARF6 and Rho family members. Apoptotic bodies may be isolated via phophatidyl-serine and membrane related markers from their parent cells. Oncosomes may be isolated by cancer specific bio-markers. Migrasomes may be isolated via the presence of integrins or markers associates with the retraction fibres of the migrating cells.

In order to determine the levels of the relevant populations of cells and/or extracellular vesicles, various methods may be utilised that are dependent on detecting the relevant cell-associated and/or vesicle-associated molecules corresponding to CD138, CD34, P-gp, PS and/or CD41a. The levels of the relevant populations of cells and/or extracellular may be determined by any assay that relies on detecting CD138, CD34, P-gp, PS and/or CD41a proteins and fragments thereof and/or mRNA that encodes CD138, CD34, P-gp, PS and/or CD41a and fragments thereof.

The methods of the present invention may rely on molecules that bind specifically to epitopes on CD138, CD34, P-gp, PS and/or CD41a molecules, such as, for example, antibodies and other affinity peptides, as well as molecules that may bind and/or hybridize to nucleic acids. Methods involving antibodies may collectively be referred to as immunoaffinity methods. The sample comprising the cells and/or plasma-cell derived microparticles, either whole, ruptured, lysed or combinations thereof, can be subjected to further selection and/or detection steps using antibodies directed towards cell surface and/or microparticle-associated proteins to determine the levels of the relevant populations.

The antibodies that bind specifically to CD138, CD34, P-gp, PS and/or CD41a may be detected directly or via molecules, such as secondary antibodies, which bind specifically to CD138, CD34, P-gp, PS and CD41a antibodies (i.e., the primary antibodies).

The primary and/or secondary antibodies may be used to capture, isolate, count and/or detect, in a sample, cells and/or extracellular vesicles that are, for example, $CD138^-/P\text{-}gp^+$, $CD138^-/P\text{-}gp^+/CD34^+$, $CD138^-/P\text{-}gp^+/PS^+$, $CD138^-/P\text{-}gp^+/CD34^+/PS^+$, $CD138^-/P\text{-}gp^+/CD41a$, $CD138^-/P\text{-}gp^+/CD34^+/CD41a^-$, $CD138^-/P\text{-}gp^+/PS^+/CD41a^-$, and/or $CD138^-/P\text{-}gp^+/CD34^+/PS^+/CD41a^-$, thereby allowing the determination of the level of said cells and/or extracellular vesicles in the sample.

The levels of the relevant populations of cells and/or extracellular vesicles may be determined by any immunoaffinity or capture assay that relies on the detecting CD138, CD34, P-gp, PS and/or CD41a with affinity molecules.

These methods used to capture, isolate, count and/or detect the cells and/or extracellular vesicles using affinity molecules such as antibodies would be well known to those skilled in the art and include, for example, affinity pulldowns, Western blot analysis, dot blot analysis, radio-immune assays, flow cytometry, FACS analysis, magnetic beads, ELISA, immunofluorescence and affinity chromatography. The skilled addressee would appreciate that some or all of these methods may be utilised quantitatively and/or qualitatively (i.e., using FACS analysis to determine numbers on cells and/or vesicles, or merely to identify and/or isolate a particular population; using western blot analysis to determine the levels of a protein or fragments thereof in a sample by densiometric analysis of bands, or merely to determine the presence or absence of a protein or fragment thereof).

The methods of the invention may also rely on the detection of mRNA or fragments thereof using methods such as northern blot analysis, nuclease protection assays, in situ hybridization and RT-PCR.

Populations of extracellular vesicles that have been captured or isolated may also be quantified via any other method known to those skilled in the art, including, but not limited to, electron microscopy, optical single particle tracking and resistive pulse sensing.

Definitions

Unless the context clearly requires otherwise, throughout the description and the claims, the words "comprise", "comprising" and the like are to be construed in an inclusive sense as opposed to an exclusive or exhaustive sense; that is to say, in the sense of "including, but not limited to".

In the context of this specification, the term "about" can mean within 1 or more standard deviation per the practice in the art. Alternatively, "about" can mean a range of up to 20%. When particular values are provided in the specification and claims the meaning of "about" should be assumed to be within an acceptable error range for that particular value.

In the context of this specification, where a range is stated for a parameter it will be understood that the parameter includes all values within the stated range, inclusive of the stated endpoints of the range.

In the context of the present invention, the term "patient" refers to an animal, preferably a mammal, most preferably a human, who has experienced and/or exhibited at least one symptom associated with a cancer. Typically, the patient is an individual having cancer and is under the clinical care of a medical practitioner. The patient may be human or may be a non-human such that reference to a patient or individual means a human or a non-human, such as an individual of any species of social, economic or research importance including but not limited to members of the classifications of ovine, bovine, equine, porcine, feline, canine, primates, rodents, especially domesticated members of those classifications, such as sheep, cattle, horses and dogs. Further, as used herein, a "patient in need thereof" may additionally be a patient who has not exhibited any symptoms of a cancer, but who has been deemed by a physician, clinician or other medical profession to be at risk of developing cancer. For example, the patient may be deemed at risk of developing cancer (and therefore in need of prevention or preventive treatment) as a consequence of the patient's medical history, including, but not limited to, family history, pre-disposition, co-existing/contributory cancer.

BRIEF DESCRIPTION OF THE DRAWINGS

Embodiments of the invention will now be described, by way of example only, with reference to the accompanying drawings as follows.

DETAILED DESCRIPTION OF PREFERRED EMBODIMENTS

Figure 1:
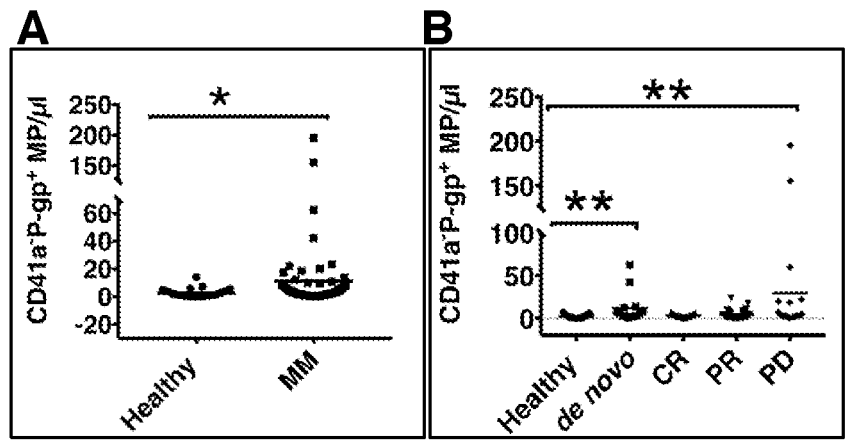
FIG. 1: P-gp$^+$ microparticle increases in multiple myeloma. The P-gp$^+$ microparticle counts in the total microparticle (CD41a$^-$) population in multiple myeloma patients and healthy subjects were determined using Tru-Count™ beads (A) P-gp$^+$ microparticle counts were significantly greater in the multiple myeloma patients (n=69) relative to healthy volunteers (n=25), p<0.01 (). (B) P-gp$^+$ microparticle counts were greater in patients in de novo (n=14) and progressive disease (PD, n=17) relative to healthy volunteers, (p<0.01 ()). There was no significant difference in the P-gp$^+$ microparticle count of healthy volunteers compared to patients in partial remission (PR, n=32) and complete remission (CR, n=13). P values were generated using Mann-Whitney U test and the data is represented as mean.

Preferred embodiments of the invention will now be described, by way of example only, with reference to the accompanying drawings.

Example 1

Reagents & Antibodies

Annexin V-V450 (BD Horizon™), anti-CD138-APC (clone M115), anti-CD41a-PE (clone HIP8), anti-P-gp-FITC (clone 17F9), anti-CD34-PE-Cy7 (clone 8G12 Y7), matched isotype controls BD™ CompBead anti-mouse-Ig k, Sphero™ Rainbow calibration particles and TruCount™ tubes were from BD Biosciences Australia. Latex beads of diameter 0.3 (cat. no. LB3) & 1.1 (cat. no. LB11) μm were purchased from Sigma-Aldrich, Australia.

Study Design and Patients

This study was approved by the Sydney Local Health District (SLHD)-Human Research Ethics Committee (HREC) of Concord Repatriation General Hospital (CRGH) [(HREC/11/CRGH/223-CH62/6/2011-150], Royal Prince Alfred Hospital (RPAH) HREC (SSA/12/RPAH/10) and the University of Technology Sydney (2012-004R). Blood samples were collected from multiple myeloma patients and healthy volunteers (>18 years of age) after informed consent at the CRGH and RPAH blood collection centres in accordance with the Declaration of Helsinki. The subjects were de-identified and assigned a code for accessing clinical information. Healthy volunteers were age-matched, non-cancer patients with normal hematology and devoid of any cytotoxic treatment or radiotherapy of any nature in the past 5 years. Pregnancy was also an exclusion criterion. In total, 25 normal subjects and 74 multiple myeloma subjects were assessed, which included treatment responsive (n=32, n=15 for partial remission and complete remission respectively), de novo (n=14) and relapsed (n=18) multiple myeloma patients. Patient responses were determined according to IMWG guidelines.

Isolation and Flow Cytometric Detection of Microparticles.

Platelet free plasma (PFP) was prepared as described previously. PFP was divided into 200 μl aliquots, which were subjected to direct immunolabeling or microparticle isolation by ultracentrifugation at 18,890×g, 4° C. for 30 min. The supernatant was removed and the microparticle pellet was immunolabeled for flow cytometry in technical triplicates for each patient microparticle count. Latex beads of 0.3 and 1.1 μm diameters were prepared and used according to the manufacturer's recommendation to define the microparticle gate and was applied to all samples during analysis (26). Flow cytometric analyses were conducted using LSRII flow cytometer/LSR Fortessa X20 and the CellQuest Pro, FACSDiva analysis software (BD Biosciences).

Surface Phenotyping of Systemic Microparticles and Quantitation.

Cell surface antibodies directed against CD138, CD41a, CD34, P-gp and phosphatidylserine were added to the microparticle pellet as previously described. Relevant isotype-matched and unstained controls were run in parallel. Platelet derived microparticles were excluded during the analysis using anti-CD41a-PE. microparticles were re-suspended in 500 μL PBS and quantitated using BD Tru-Count™ beads as previously described.

Statistical Analysis

Mann-Whitney (U) test was conducted for the non-parametric data using GraphPad Prism® version 7.0 for Mac (GraphPad, La Jolla, Calif., USA). The data presented as the mean and Mann-Whitney constant U. The results with a predictive value of (*) $P<0002$, () $P<0.01$ and (*) $P<0.05$ were considered significant.

Results

P-gp$^+$ Microparticle Numbers are Elevated in De-Novo and Progressive Disease Multiple Myeloma Patients.

It was observed that significantly greater numbers of P-gp$^+$ microparticles were present in the total (CD41a$^-$) microparticle population in multiple myeloma patients relative to healthy volunteers (FIG. 1A). The absolute number of P-gp$^+$ microparticles from multiple myeloma patients was 5.1 fold greater number per μl relative to the healthy volunteers (U=605, p<0.01). Specifically, it was observed that there was a 5.67 (U=70, p<0.01) and 12.4 (U=104, p<0.01) fold increase in P-gp$^+$ microparticles for de novo and progressive disease (PD), respectively, relative to the healthy volunteers (FIG. 1B). There was no significant difference between P-gp$^+$ microparticles between healthy volunteers and patients in complete (CR) or partial remission (PR) (FIG. 1B).

CD138$^+$ Microparticles do not Express Significant Levels of P-gp on their Surface.

Figure 2:
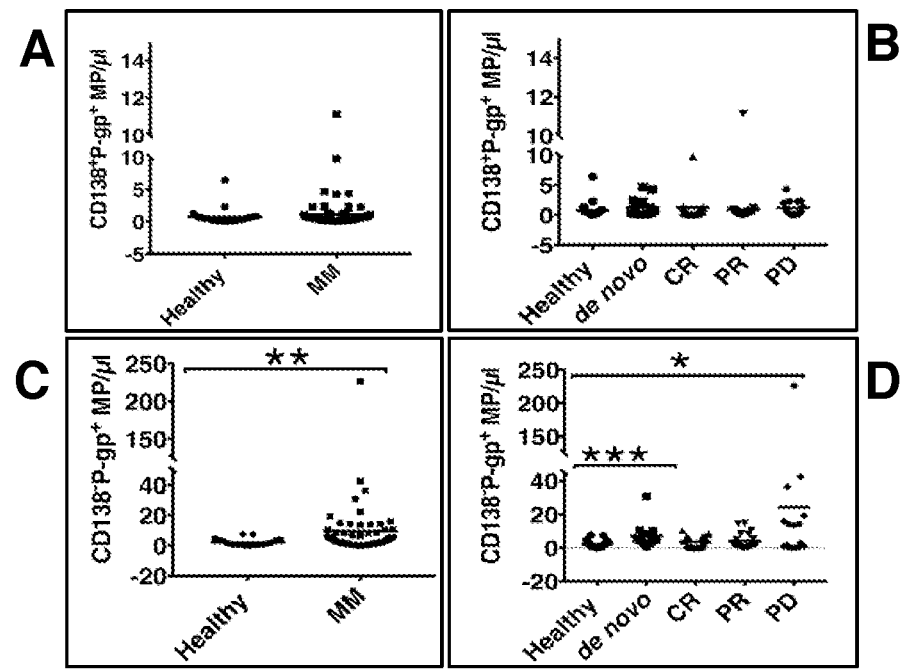
FIG. 2: CD138$^+$ microparticles do not significantly express P-gp. (A) The CD133$^+$ P-gp$^+$ microparticle count was elevated in multiple myeloma relative to healthy volunteers however was not significant in a CD133$^+$ microparticle population. (B) Consequently, CD133$^+$ P-gp$^+$ microparticle count across de novo (n=14), PR (n=32), CR (n=13) and PD were elevated though not significant. (C) The CD138$^-$ P-gp$^+$ microparticle count was significantly elevated in multiple myeloma patients relative to healthy volunteers (n=25) (p<0.01 ()). (D) CD138$^-$ P-gp counts were significantly higher in de novo cohort (P=0.0002 (*)) and PD (p<0.05 (*)) however was not significant for CR, PR. P values were generated using Mann-Whitney U test and the data is represented as mean.

P-gp expression on the CD133$^+$ microparticle population in multiple myeloma patients was not significantly increased compared with the healthy volunteers (U=716, p=0.28) (FIG. 2A). There was no significant increase observed across de novo, CR, PR and PD subpopulations (FIG. 2B) respectively relative to healthy volunteers.

In contrast, P-gp expression on the CD138$^-$ microparticles showed a significant 4.5 fold increase relative to healthy volunteers (U=553, p=0.009, FIG. 2C). The P-gp$^+$/CD138$^-$ microparticle numbers were 3.6 fold higher in the de novo cohort (U=57, p=0.0003) and 12.2 fold in PD relative to the healthy volunteers (U=126, p=0.04). The absolute numbers were not significantly different in the CR (U=151, p=0.19) or PR (U=195, p=0.14) cohorts compared to the healthy volunteers. (FIG. 2D).

Example 2

Five individual patients across all disease states were selected and their microparticles phoenotyped for the presence P-gp, CD34 and CD138. CD34 is a transmembrane protein belonging to the CD34 family of sialomucins and is an established haematopoietic stem cell marker. Although, not typically used in phenotyping plasma cells, CD34 is present on a minor subpopulation of multiple myeloma stem cell clones. The selected panel of individual patients included (a) aggressive disease, patient 1 (b) progressive disease, patient 2 (c) stable disease, patient 3 (d) partial remission, patient 4 and (e) a long-term survivor in remission, patient 5. We also phenotyped microparticles for the extent of phosphatidylserine (PS) using annexin V. PS is expressed preferentially on the surface of microparticles of cancer cells of 'stem cell like' origin. PS on microparticles has been recently shown to be required for interactions with vascular endothelial cells in neovascularisation and is associated with cancer progression.

Case 1: 58-Year-Old Female Patient with Aggressive Disease.

Figure 3:
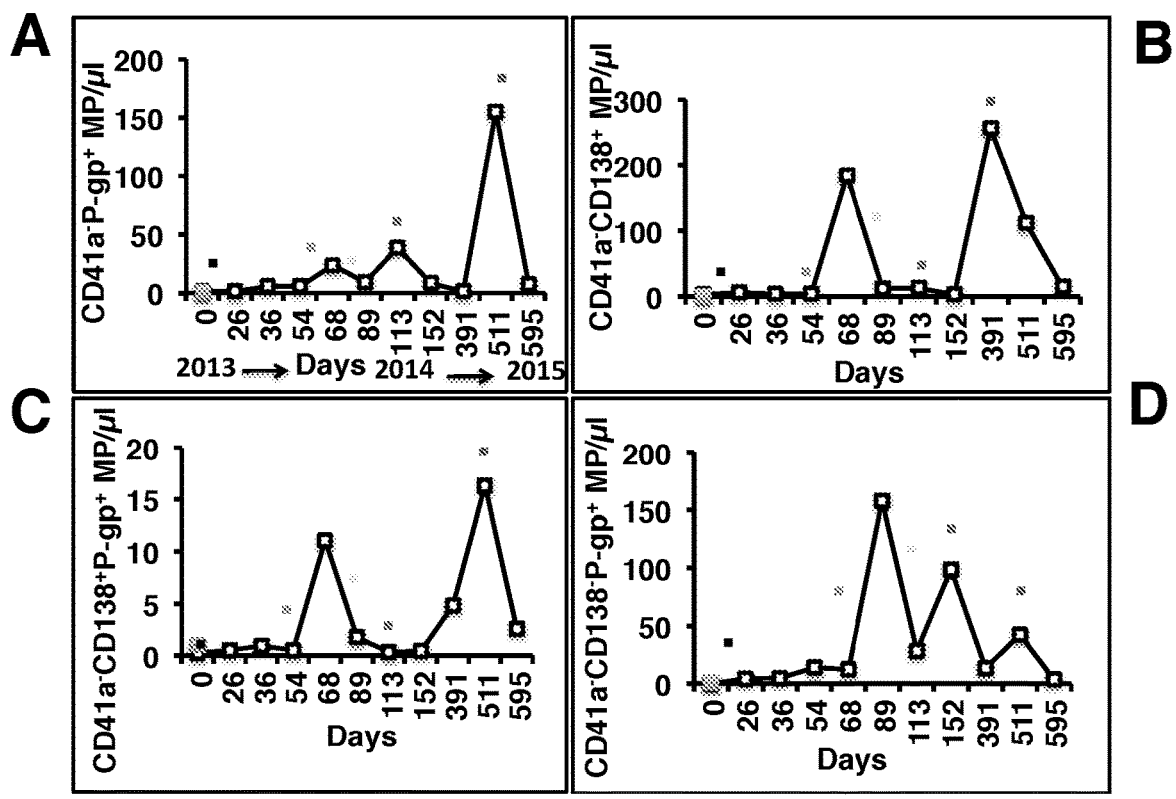
FIG. 3: P-gp$^+$ microparticles in a 56-year-old patient with aggressive disease during the course of treatment (patient 1) microparticles were isolated from the PFP of a 56-year-old multiple myeloma patient at diagnosis and during the course of treatment. The absolute P-gp$^+$ microparticle counts (Y-axis) and time of microparticle sampling post diagnosis (X-axis) are shown. (A) (CyBorD, black dot; BorD, pink dot; VTD, blue dot lenalidomide/dexamethasone, red dot and D-PACE and melphalan, green dot) (B) CD41a$^-$ CD133$^+$ microparticle profile of the patient 1 (C) Corresponding CD41a$^-$ CD133$^+$ P-gp$^+$ and (D) CD41a$^-$ CD133$^+$ P-gp$^+$ microparticle profiles of patient 1.

FIG. 3A-D demonstrates the serial P-gp$^+$ microparticle count of a 58-year-old female patient (patient 1) who was diagnosed with IgG multiple myeloma in September 2013 with 86% plasmacytosis in the bone marrow aspirate. At diagnosis, the P-gp$^+$ microparticle count was minimal. Induction therapy with cyclophosphamide, bortezomib, dexamethasone (CyBorD) commenced in September 2013 (FIG. 3 black dot) but in November 2013 cyclophosphamide was withdrawn due to severe anaemia (FIG. 3 pink dot). A bone marrow biopsy in December 2013 showed partial response with 46% plasmacytosis. During this time, the number of P-gp$^+$ microparticle was increasing steadily which was consistent with the emergence of MDR. Thalidomide was added from January-April 2014 (FIG. 3, blue dot). A follow up biopsy showed reduced plasmacytosis of 23% in April 2014 (~days 70-80). The paraprotein increased to 38.3 g/l (progressive disease) in June-July 2014 and the treatment regimen changed to lenalidomide/dexamethasone from July-October 2014 (~100 days) (FIG. 3 red dot). Patient 1 relapsed with a right side posterior mass along the chest wall in early February 2015 (60% plasmacytosis, around 130 days) while the M-protein level was only 18 g/l at that point in time (data not shown). At this time, P-gp$^+$ microparticles in PFP continued to significantly increase. Dexamethasone along with platinol, adriamycin, cyclophosphamide and etoposide (D-PACE) and melphalan added to treatment regimen at this point (FIG. 3 green dot) and patient 1 achieved partial remission (~day 495). She had a successful autologous stem cell transplant in July 2015. However, she relapsed soon and became unresponsive to all therapy in November 2015 and passed away in December. FIG. 3B shows the profile of P-gp$^+$/CD138$^+$ microparticles in the same patient. Consistent with our previous findings, the levels of these microparticles correspond to disease burden and treatment outcome (FIG. 3B). In the context of counts, the CD138$^+$ microparticle subtype was not the predominant P-gp$^+$ population (FIG. 3C). Rather the predominant Pgp$^+$ microparticle subtype was CD138$^-$ (FIG. 3D). Upon examining the microparticle profiles for annexin V$^+$ sub populations in patient 1, a significant difference in the levels between the CD138$^+$ and CD138$^-$ subtypes was not observed (data not shown).

Figure 4:
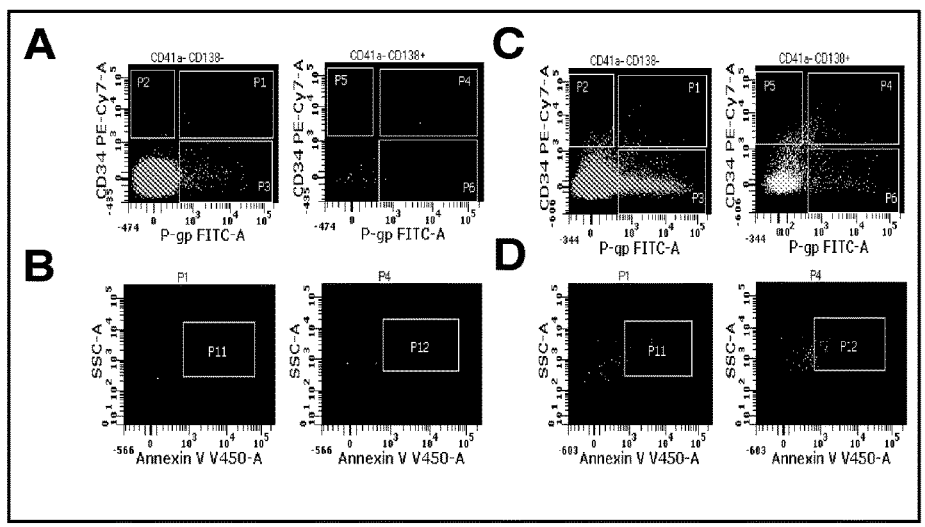
FIG. 4: Isotype-matched control to define parameters for $^{+/-}$ staining patient 1 in partial remission and 'dual positive' population in May 2015. CD138$^{+/-}$ population was gated based on anti CD138$^-$APC$^{+/-}$ staining for patient 1 in PR. Isotype-matched control was used to define gating parameters for positive and negative staining for CD138$^-$ P-gp$^+$ CD34$^+$ (4A, left panel) and CD138$^+$/P-gp$^+$/CD34$^+$ (4A, right panel) for patient 1 in PR (B) Gates were defined for CD138$^-$ CD34$^+$ annexin V$^+$ (4B, left panel) and CD138$^+$/ CD34$^+$ annexin V$^+$ (4B, right panel) for patient 1 in PR. (C) microparticles were phenotyped patient 1 in partial remission status for the presence of 'dual positive' population based on CD138$-/^+$ staining. We assessed the presence of P-gp, CD34 in CD138$^-$ (red events) and CD138$^+$ (blue events) microparticle sub-sets by flow cytometry (4C, left and right panel respectively). (D) microparticles were also phenotyped for the levels of PS enrichment using annexin V in the in CD138⁻ (4D, left panel, yellow events) and CD138⁺ subpopulation of microparticles (4D, right panel, orange events).
Figure 5:
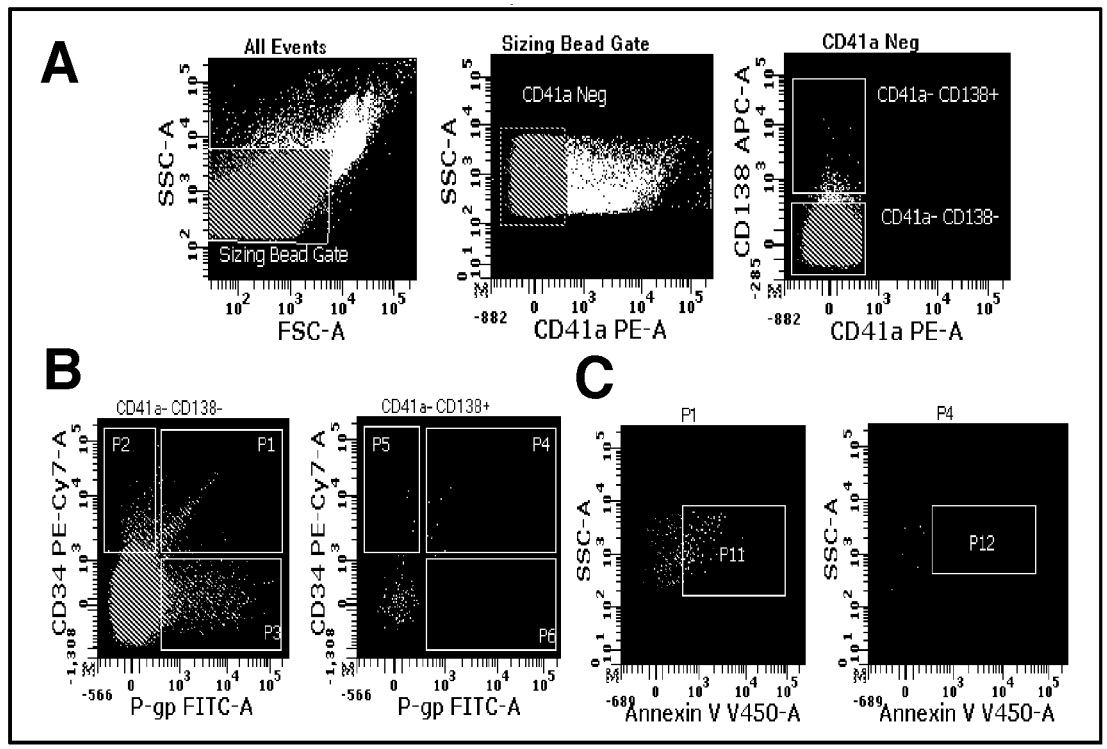
FIG. 5: Elevated levels of 'dual positive' microparticles in patient 1 with aggressive disease. The presence of P-gp and CD34 in CD138⁻ (red events) and CD138⁺ (blue events) microparticle subpopulations was established by flow cytometry in patient 1. (A) A sequential gating strategy using microparticle size gate (left panel) followed by gating for CD41a (middle panel) and CD138 (right panel) was applied to the total microparticle population (left panel). The CD41a⁻ population was defined based on ⁺/⁻ staining for anti-CD41a⁻ PE (middle panel). (B) The total population (CD41a⁻) was gated based on CD138–/⁺ staining (left panel, red events, right panel, blue events, respectively). Within this microparticle population, we phenotyped for CD138⁻/P-gp⁺/CD34⁺ (left panel, gate P1) population and CD138⁺ P-gp⁺ CD34⁺ sub-population (right panel, gate P4). (C) The CD138 microparticle subtypes (gate P1 & P4 of left and right panel respectively). The CD138 microparticle subtypes (gate P1 & P4 of left and right panel respectively) were gated and phenotyped for the presence PS exposure using annexin V (left panel, gate P11, yellow events) (right panel, gate P12, orange events) respectively.

A blood sample was taken from patient 1 on 11 Feb. 2015 during progressive disease and prior to stem cell transplantation. This sample showed elevated numbers of CD34$^+$ (496.81/μl) and P-gp$^+$ (155.29/μl) total CD41a$^-$ microparticle events (Table 1) compared to that observed when the patient was in partial remission in May 2015 (7.33/μl and 6.31/μl for CD34$^+$ and P-gp$^+$, respectively, FIG. 4). Gating parameters were established to detect CD41a$^-$ events in the context of CD138 and are shown in FIG. 5A. The levels of CD34$^+$ and P-gp$^+$ microparticle events within CD138$^+$ (red) and CD138$^-$ (blue) microparticle subtypes (FIGS. 4B and C) were compared. The predominant population which was P-gp$^+$ and CD34$^+$ was the CD138$^-$ microparticle subtype (referred to as the 'dual positive' population for simplicity) FIG. 5B, left panel, gate P1, 12.48/μl). Very little P-gp$^+$/CD34$^+$/CD138$^+$ microparticles (FIG. 5B, right panel, gate P4, 0.30/μl) was detected. Additional microparticle sub-sets which were CD138$^-$/P-gp$^+$/CD34$^-$ (FIG. 4B, left panel, gate P3, 56.45/μl) and CD138$^+$/P-gp$^-$/CD34$^+$ microparticle (FIG. 5B, right panel, gate P2, 28.5/μl) were also detected microparticles within the CD138$^+$ population that were solely CD34$^+$ and P-gp$^+$ were not detected (FIG. 5B, right panel, gate P5 and P6).

The CD138 microparticle subtypes were gated and phenotyped for the presence PS exposure using annexin V. The presence of annexin V$^+$ microparticles (FIG. 5C, left panel, gate P11, 5/μl) within the CD138$^+$/P-gp$^+$/CD34$^-$ microparticle population was detected. In contrast, annexin V positive events on CD138$^+$/P-gp$^+$/CD34$^+$ microparticles were not detected (FIG. 5C, right panel, gate P12, 0 events) (Table 1).

In summary, this patient with an aggressive disease course demonstrated significantly elevated levels of P-gp on microparticles of 'stem cell like' origin (i.e. CD138$^-$/P-gp$^+$/CD34$^+$). A small proportion of this population also was positive for PS.

Case 2: 66-Year-Old Female Patient in Progressive Disease

Figure 6:
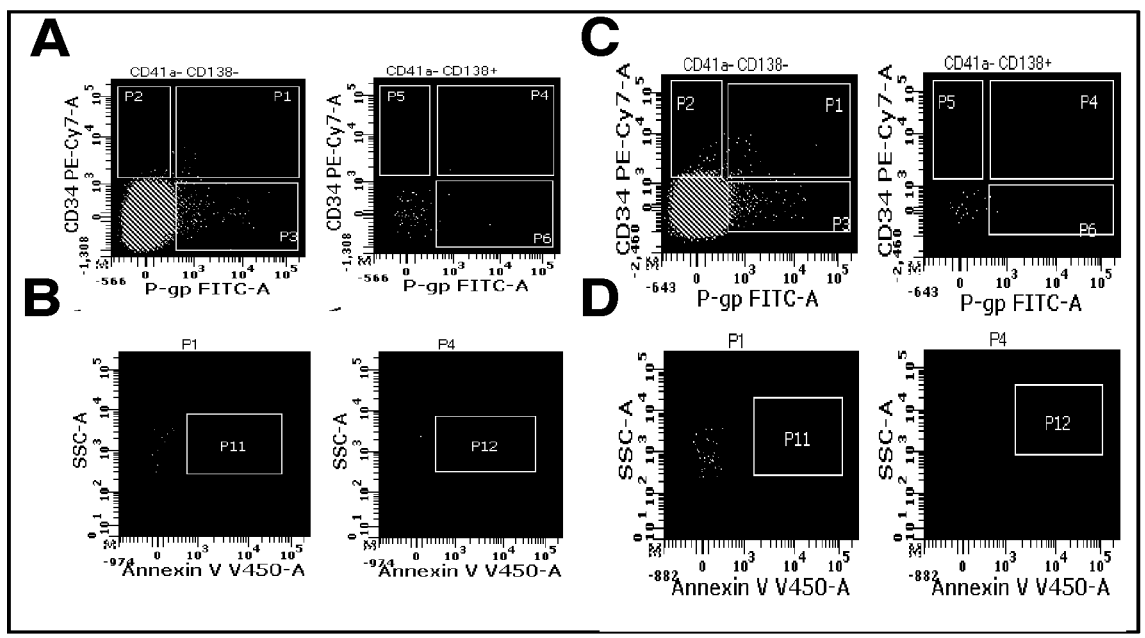
FIG. 6: Isotype-matched control to define parameters for ⁺/⁻ staining in patient 2 (PD) and 3 (stable). (A) CD138⁺/⁻ population was gated based on anti-CD138⁻/APC ⁺/⁻ staining for patient 2 and 3. Isotype-matched control was used to define gating parameters for positive and negative staining for CD138⁻/P-gp⁺/CD34⁺ (2A, left panel) and CD138⁺/P-gp⁺/CD34⁺ (2A, right panel) for patient 2 (B) Gates were defined for CD138⁻/CD34⁺/annexin V⁺ (2B, left panel) and CD138⁺/CD34⁺/annexin V⁺ (2B, right panel) for patient 2 (C) Isotype-matched control was used to define gating parameters for positive and negative staining for CD138⁻/P-gp⁺/CD34⁺ (2C, left panel) and CD138⁺/P-gp⁺/CD34⁺ (2C, right panel) for patient 3 (D) Gates were defined for CD138⁻/CD34⁺/annexin V⁺ (2D, left panel) and CD138⁺/CD34⁺ annexin V⁺ (2D, right panel) for patient 3.
Figure 7:
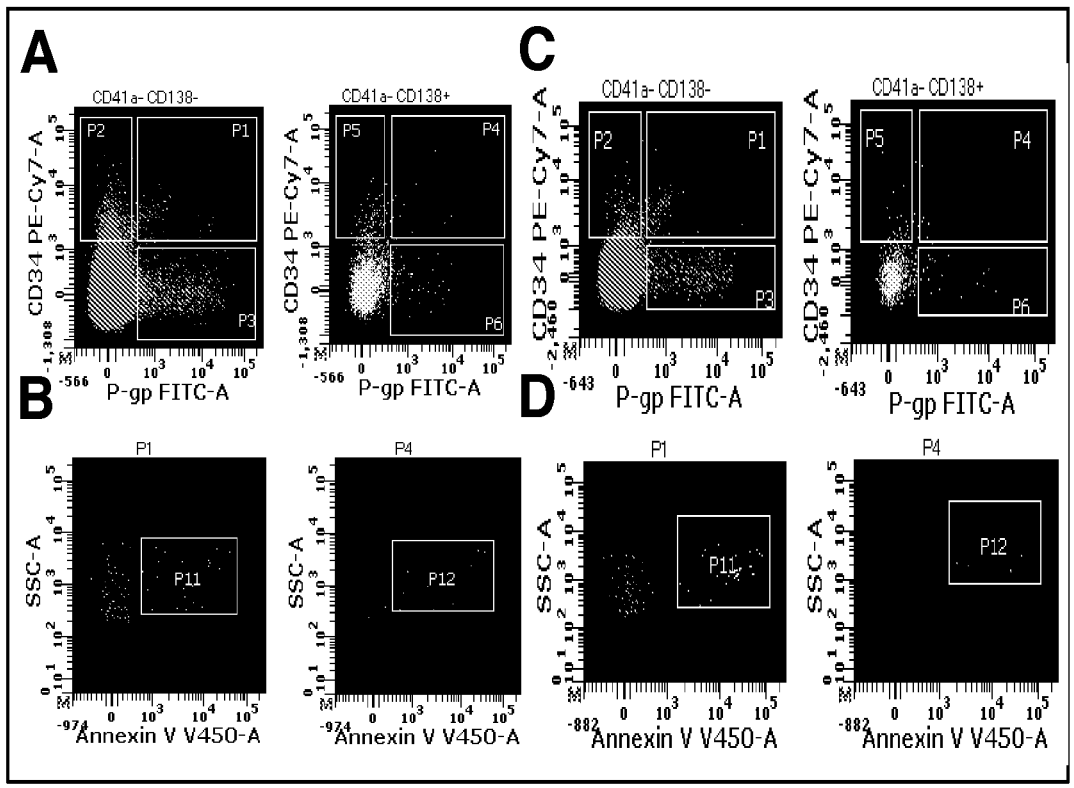
FIG. 7: 66-year-old female patient in progressive disease (patient 2) and 63-year-old male patient (patient 3) in stable condition. The presence of P-gp and CD34 in CD138⁻ (red events) and CD138⁺ (blue events) microparticle subpopulations was established by flow cytometry in patient 2 and 3. (A) The total population (CD41a⁻) was gated based on CD138–/⁺ staining (left panel, red events, right panel, blue events, respectively). Within this microparticle population, we phenotyped for CD138⁻/P-gp⁺/CD34⁺ (left panel, gate P1) population and CD138⁺/P-gp⁺/CD34⁺ sub-population (right panel, gate P4). (B) The CD138 microparticle subtypes (gate P1 & P4 of left and right panel respectively) were gated and phenotyped for the presence PS exposure using annexin V (left panel, gate P11, yellow events) (right panel, gate P12, orange events) respectively.

A 66-year-old female patient (patient 2) was diagnosed with kappa light chain myeloma in 2014. She was enrolled and treated in a clinical trial MLN9708 (cyclophosphamide/dexamethasone) from December 2014 until March 2015, which was stopped in February 2015 due to progressive disease with a rise in kappa light chains. At the time of sampling on 5 May 2015, she was on CyBorD therapy for her progressive disease. During this time it was observed that CD34$^+$ (40.5/μl) and P-gp$^+$ microparticle events (60/μl) within the total (CD41a$^-$) microparticles (Isotype-matched control; FIG. 6) were present. Within this population, the presence of a CD138$^-$/P-gp$^+$/CD34$^+$ population (FIG. 7A, left panel, gate P1, 4.6/μl) and a CD138$^+$/P-gp$^+$/CD34$^+$ population was detected (FIG. 7A, right panel, gate P4, 0.5/μl). A sub-set of CD138$^-$/P-gp$^+$/CD34$^-$ microparticles (FIG. 7A, left panel, gate P3, 58.8/μl) and CD138$^+$/P-gp$^-$/CD34$^+$ was also detected (FIG. 7A, right panel, gate P6, 3/μl).

The CD138 microparticle subtypes were gated and phenotyped for the presence PS exposure using annexin V. A minimal presence of CD138$^-$/P-gp$^+$/CD34$^+$ annexin V$^+$ microparticles (FIG. 7B, left panel, gate P11, 1.1/μl) in this patient at this given point in time was detected. CD138$^+$/P-gp$^+$/CD34$^+$ annexin V$^+$ microparticle levels were also minimal (FIG. 7B, right panel, gate P12, 0.4/μl) (Table 1).

In summary, compared to patient 1, this patient with progressive disease demonstrated lower levels of the 'dual positive' population and showed only minimal positivity with PS.

Case 3: 63-Year Male Patient in Stable Condition

A 63-year-old male in a stable disease state (patient 3) at the time of sampling was diagnosed with IgG kappa multiple myeloma 2011 (smoldering myeloma 2008, active myeloma July 2011). The induction therapy consisted of 6 cycles of cyclophosphamide, thalidomide and dexamethasone followed by autologous stem cell transplant on 30 Mar. 2012. The patient experienced severe peripheral neuropathy associated with thalidomide and an increase in serum paraprotein, which resulted in a treatment change to lenalidomide, and dexamethasone July 2012. At the time of sampling in May 2015, the patient was on lenalidomide and dexamethasone, zometa and aspirin.

The patient presented with CD34$^+$ (5.13/μl) and P-gp$^+$ (6.3/μl) microparticles in total microparticles (CD41a$^-$) at the time of sampling (Isotype-matched control; FIG. 6). Within this population, the presence of CD138$^-$/P-gp$^+$/CD34$^+$ population (FIG. 7C, left panel, gate P1, 4.7/μl) and CD138$^+$/P-gp$^+$/CD34$^+$ (FIG. 7C, right panel, gate P4, 0.2/μl) was detected. A sub-set of CD138$^-$/P-gp$^+$/CD34$^-$ (FIG. 7C, left panel, gate P3 23.13/μl) and CD138$^-$/P-gp$^-$/CD34$^+$ (FIG. 7C, left panel, gate P2, 18.54/μl) was also found. A sub-set of CD138$^+$/P-gp$^+$/CD34$^+$ (FIG. 7C, right panel, gate P5, 1.2/μl) CD138$^+$/P-gp$^+$/CD34$^-$ (FIG. 7C, right panel, gate P6, 1/μl) was also observed.

The CD138 microparticle subtypes were gated and phenotyped for the presence PS exposure using annexin V. The presence of CD138$^-$/P-gp$^+$/CD34$^+$ annexin V$^+$ microparticles (FIG. 7D, left panel, gate P11, 1.6/μl) in this patient at this given point in time and CD138$^+$/P-gp$^+$/CD34$^+$ annexin V$^+$ microparticle (FIG. 7D, right panel, gate P12, 0.3/μl events) (Table 1) was observed.

In summary, the 'dual positive' population was present in comparable levels in patient 3 relative to patient 2. The sub-set was also not significantly enriched with PS.

Case 4: 71 Year Old Male Patient in Partial Remission

Figure 8:
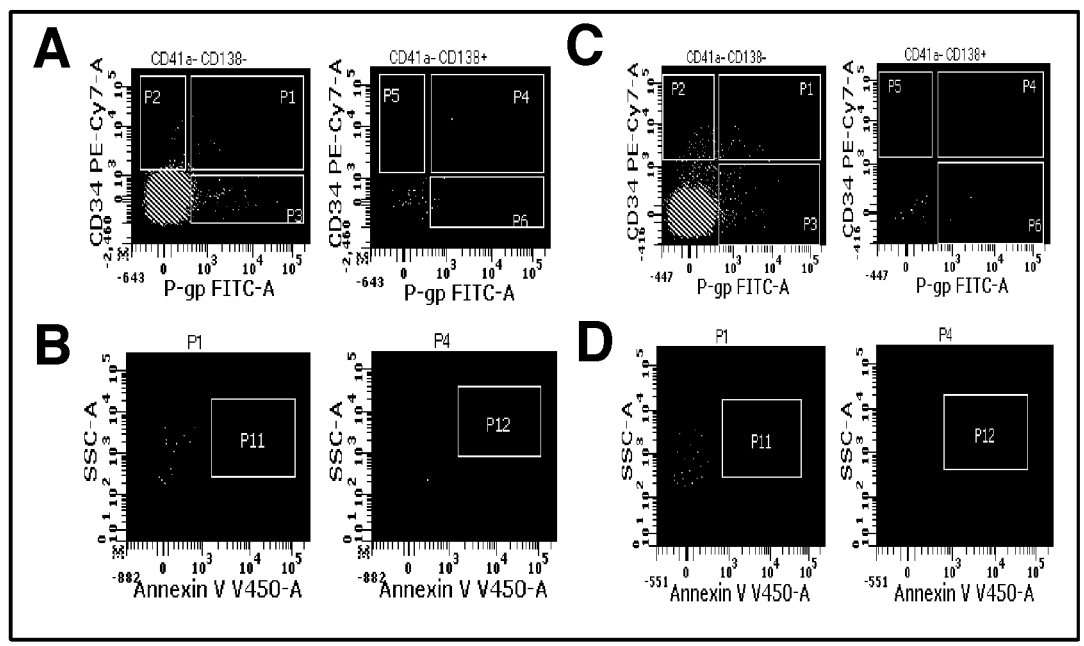
FIG. 8: Isotype-matched control to define parameters for ⁺/⁻ staining in patient 4 (PR) and 5 (remission). (A) CD138⁺/⁻ population was gated based on anti CD138–APC⁺/⁻ staining for patient 4 and 5. Isotype-matched control was used to define gating parameters for positive and negative staining for CD138⁻/P-gp⁺/CD34⁺ (3A, left panel) and CD138⁺/P-gp⁺/CD34⁺ (3A, right panel) for patient 4 (B) Gates were defined for CD138⁻/CD34⁺/annexin V⁺ (3B, left panel) and CD138⁺/CD34⁺/annexin V⁺ (3B, right panel) for patient 4 (C) Isotype-matched control was used to define gating parameters for positive and negative staining for CD138⁻/P-gp⁺/CD34⁺ (3C, left panel) and CD138⁺/P-gp⁺/CD34⁺ (3C, right panel) for patient 5 (D) Gates were defined for CD138⁻/CD34⁺/annexin V⁺ (3D, left panel) and CD138⁺/CD34⁺/annexin V⁺ (3D, right panel) for patient 5.

A 71-year-old male (patient 4) was diagnosed on February 2014 following a biopsy of a right shoulder mass. He presented with widely disseminated skeletal disease with multiple lesions as evidenced by positron emission tomography scan. Induction therapy consisted of CyBorD treatment from April 2014. The patient achieved very good partial remission after 6 cycles and treatment was stopped at 6 cycles instead of 8 due to severe peripheral neuropathy resulting from bortezomib. The sample analyzed was taken on 12 Aug. 2014. It was observed that numbers of CD34$^+$ (15.13/μl) and P-gp$^+$ microparticle events (10/μl) within the total (CD41a$^-$) microparticle population (Isotype-matched control; FIG. 8). Within this population, the presence of CD138⁻/P-gp⁺/CD34⁺ population (FIG. 9A, left panel, gate P1, 7.2/µl) and CD138⁺/P-gp⁺/CD34⁺ (FIG. 9A, right panel, gate P4, 0.5/µl) was detected, and a sub-set of CD138⁻/P-gp⁺/CD34⁻ (FIG. 9A, right panel, gate P3, 36.53/µl) and CD138⁻/P-gp⁻/CD34⁺ (FIG. 9A, left panel, gate P2, 63.17/µl) was found in this sample. A very small sub-set of CD138⁺/P-gp⁻/CD34⁺ (FIG. 9A, right panel, gate P5, 4/µl) and CD138⁺/P-gp⁺/CD34⁻ (FIG. 9A, right panel, gate P6, 2.2/µl) was also observed.

The CD138 microparticle subtypes were gated and phenotyped for the presence PS exposure using annexin V. The presence of CD138⁻/P-gp⁺/CD34⁺ annexin V⁺ microparticles (FIG. 9B, left panel, gate P11, 2.5/µl) was detected and CD138⁺/P-gp⁺/CD34⁺ annexin V⁺ microparticle was negative (FIG. 9B, right panel, gate P12, 0 events) (Table 1).

In summary, patient 4 demonstrated elevated albeit lower levels of the 'dual positive' population compared to that of the patient 1. The sub-set was enriched with PS however levels were lower than that detected for patient 1.

Case 5: 62 Year Old Male Patient in Remission—Long-Term Survivor

A 62-year-old male (patient 5) was diagnosed at 50 years of age with IgG kappa multiple myeloma with bone marrow biopsy showing 10-15% plasma cell infiltration. His induction regimen consisted of VAD (vincristine, adriamycin (doxorubicin) and dexamethasone). This was followed by an autologous stem cell transplant in 2007, after which he remained in an unmaintained complete remission for almost three years. He experienced a relapse in 2012 with rise in serum paraprotein albeit he had no other issues. He was given thalidomide and achieved very good partial response in early 2013 with bone marrow biopsy showing only 3% plasma cell infiltration and M-protein too low to quantitate. His M protein started to increase in late 2014 and reached 17 g/l in October 2014. The patient was subsequently enrolled and treated on a clinical trial (lenalidomide/dexamethasone plus or minus daratumumab) in December 2014. At the time of sampling the patient was responding very well and he eventually achieved stringent complete remission with ongoing chemotherapy. This patient is a long-term survivor (12 years) with successful therapeutic interventions over a long period.

Figure 9:
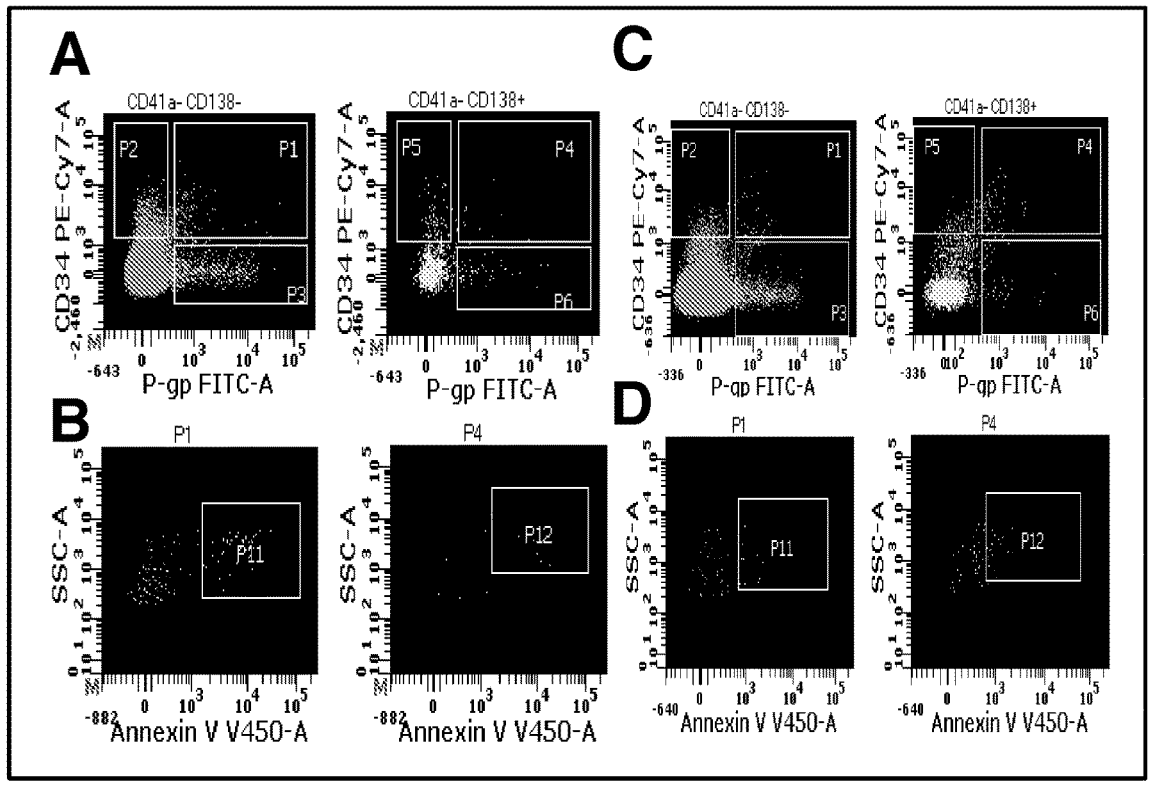
FIG. 9: 71-year-old male patient on partial remission (patient 4) and 62-year-old male patient in remission—long-term survivor (patient 5). The presence of P-gp and CD34 in CD138⁻ (red events) and CD138⁺ (blue events) microparticle subpopulations was established by flow cytometry in patient 4 and 5. (A) The total population (CD41a⁻) was gated based on CD138–/⁺ staining (left panel, red events, right panel, blue events, respectively). Within this microparticle population, we phenotyped for CD138⁻/P-gp⁺/CD34⁺ (left panel, gate P1) population and CD138⁺/P-gp⁺/CD34⁺ sub-population (right panel, gate P4). (B) The CD138 microparticle subtypes (gate P1 & P4 of left and right panel respectively) were gated and phenotyped for the presence PS exposure using annexin V (left panel, gate P11, yellow events) (right panel, gate P12, orange events) respectively.

At the time of sampling on 5 May 2015, it was observed that numbers of CD34⁺ (5.13/µl) and P-gp⁺ microparticle events (6.3/µl) within the total (CD41a⁻) microparticle population (Isotype-matched control; FIG. 8). The presence of CD138⁻/P-gp⁺/CD34⁺ population (FIG. 9C, left panel, gate P1, 2.54/µl) and CD138⁺/P-gp⁺/CD34⁺ (FIG. 9C, right panel gate P4, 3.0/µl) was detected. We also found a sub set of CD138⁻/P-gp⁺/CD34⁻ (FIG. 9C, left panel, gate P3, 52.83/µl) and CD138⁺/P-gp⁻/CD34⁺ (FIG. 9C, left panel, gate P2, 14.46/µl). A very small sub-set of CD138⁺/P-gp⁻/CD34⁺ (FIG. 9C, right panel, gate P5, 4.5/µl) and CD138⁺/P-gp⁺/CD34⁻ (FIG. 9C, right panel, gate P6, 2.4/µl) was also observed.

The CD138 microparticle subtypes were gated and phenotyped for the presence PS exposure using Annexin V. The presence of CD138⁻/P-gp⁺/CD34⁺ annexin V⁺ microparticles (FIG. 9D, left panel, gate P11, 0.5/µl) and CD138⁺/P-gp⁺/CD34⁺ annexin V⁺ microparticle (FIG. 9D, right panel, gate P12, 1.17/µl) (Table 1) was detected.

In summary, this patient demonstrated significantly reduced levels of the 'dual positive' population compared to all other disease states. There were barely detectable PS exposure on this population of microparticles.

Overall, it was observed that elevated levels of the CD138⁻/P-gp⁺/CD34⁺ microparticle sub-set in multiple myeloma patients with more severe forms of the disease.

PS⁺ Microparticle Represents a More Aggressive State in Multiple Myeloma

Figure 10:
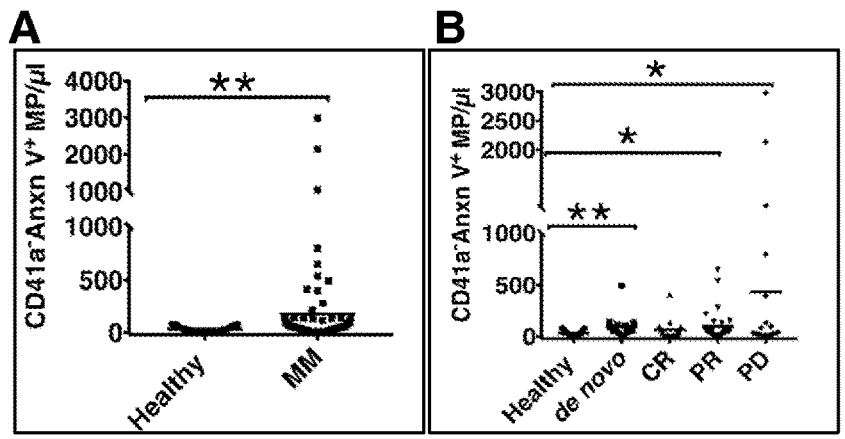
FIG. 10: PS⁺ microparticle represents a more aggressive state in multiple myeloma. The annexin V⁺ microparticle counts in multiple myeloma patients and healthy subjects were compared using Trucount™ beads. (A) PS⁺ microparticle counts were significantly greater in multiple myeloma patients (n=74) relative to healthy volunteers (n=25) $p<0.01$ (). (B) PS⁺ microparticle counts were greater in de novo (n=14), partial remission (n=31), and progressive disease (PD, n=18) relative to healthy volunteers (n=25). No significant difference in annexin V⁺ microparticle counts was observed between the CR (n=15) and healthy volunteers. P values were generated using Mann-Whitney U test and the data is represented as mean ($P<0.01$ (), $P<0.05$ (*)).

PS⁺ microparticle subpopulations within the total (CD41a⁻) microparticle population were significantly (5.6 fold) increased in multiple myeloma patients relative to the healthy volunteers (U=607, p=0.009) (FIG. 10 A). PS V⁺ microparticle counts were 3.1 fold elevated in the de novo cohort relative to healthy volunteers (U=80, p=004) while the partial remission cohort showed a 3.08 fold increase in annexin V⁺ microparticle counts (U=249, p=0.02) to that of healthy volunteers. The annexin V⁺ microparticle counts were 13.9 fold higher in the progressive disease cohort relative to healthy volunteers (U=136, p=0.02). We did not observe any significant difference in annexin V⁺ microparticle counts between the CR cohort and healthy volunteers (FIG. 10B).

PS and CD138 do not Co-Express in Progressive Disease.

Figures 11, 12:
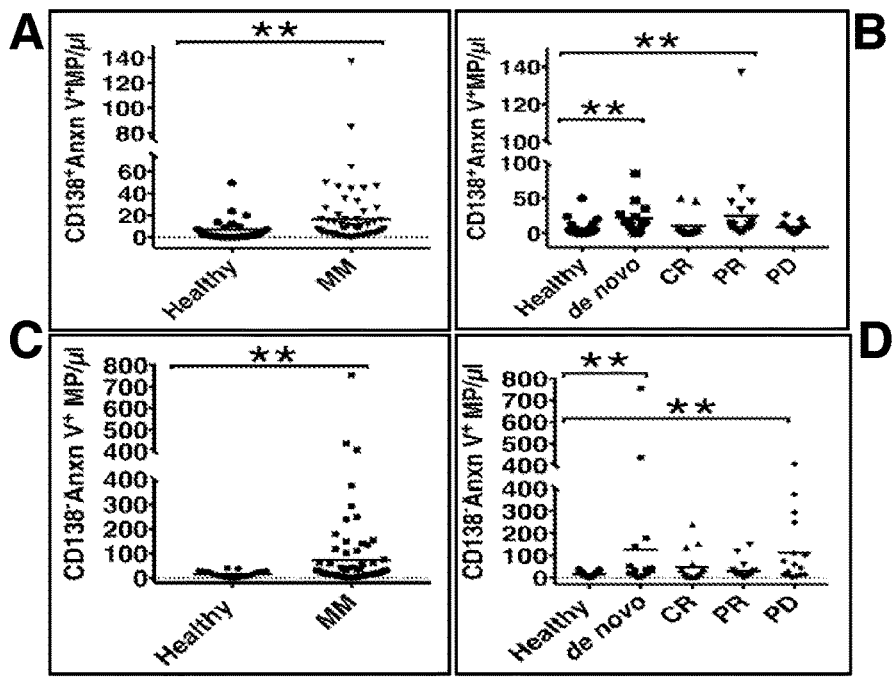
FIG. 11: PS⁺ and CD138 do not co-express in progressive disease. (A) PS microparticles in the CD133⁺ microparticle sub-set in multiple myeloma patients were significantly elevated in multiple myeloma patients compared to the healthy volunteers ($p<0.01$, ()). (B) CD138⁺/PS⁺ microparticle levels in the de novo and PR cohort were significantly higher relative to healthy volunteers ($p<0.01$, ()) while CR and PD had insignificant levels relative to healthy volunteers. (C) PS⁺ microparticles in the CD138⁻ microparticle sub-set were significantly elevated in multiple myeloma patients relative to that for healthy volunteers. (D) CD138⁻/PS⁺ microparticles were significantly higher in de novo and PD cohorts relative to healthy volunteers. There was no significant difference in CR and PR cohorts relative to healthy volunteers. Mann-Whitney U test was conducted to generate P values and the data is represented as mean ($P<0.01$ (**)).
FIG. 12: Table showing microparticle subtypes across different clinical states.

FIG. 11A shows the CD138⁺ annexin V⁺ microparticle profile of multiple myeloma patients with respect to healthy volunteers. It was observed that a significant 2.4 fold greater PS exposure in CD138⁺ microparticle sub-set for multiple myeloma patients compared to healthy volunteers (U=452.5, p=0.006). In the cohort data, the de novo and PR cohorts showed a 3.1 (U=82.5, p=0.005) and 3.61 (U=96.5, p=002) fold increase, respectively in PS exposure to that of healthy volunteers whilst it was observed that no significant difference with CR or PD cohorts relative to healthy volunteers (FIG. 11B).

FIG. 11C shows the CD138⁻ annexin V⁺ microparticle profile of multiple myeloma patients. It was observed that a significant 4.3 fold increase in PS exposure in multiple myeloma patients compared to healthy volunteers in the CD138⁻ sub-set of microparticles (U=570, P=0.009). In the cohort data, the de novo patients had a 7.73 fold higher PS exposure (U=77, p=0.003) on CD138⁻ microparticles compared to healthy volunteers while patients with PD had a 6.9 fold higher PS exposure (U=94, p=0.003) in the CD138⁻ sub-set (FIG. 11D) relative to healthy volunteers. A significant difference in PS exposure for the CR and PR cohorts with respect to healthy volunteers was not observed (FIG. 11D).

DISCUSSION

The results show that multiple myeloma patients have higher P-gp⁺ events in the total CD41a⁻ and CD138⁻ microparticle population compared to healthy volunteers, specifically in the de novo and PD cohorts. P-gp⁺ events within the total microparticle population as well as within each microparticle subtype were shown to correspond to treatment response when levels were monitored in individual patients.

While CD138 is a useful surrogate marker for plasma cells, the results showed that P-gp⁺ microparticle events in multiple myeloma patients were predominantly within the CD138⁻ population. It was observed that significantly greater P-gp⁺ microparticle events in patients with progressive disease. Within the total CD41a⁻ microparticle population we identified a number of different subtypes based on the presence of CD138 and P-gp.

Patient 2 (PD) and patient 3 (stable) had almost identical 'dual positive population'. Patient 3 was in a stable condition while patient 2 was already showing response after one cycle of bortezomib (as defined by a drop in light chain levels) at the time of sampling and correspondingly had less 'dual population' relative to patient's 1 and 4. Patient 5 had a barely detectable 'dual positive' microparticle population corresponding to the remission and long-term survivor status. This data clearly demonstrates an association between elevated levels of the 'dual positive' microparticle population and treatment unresponsiveness as well disease activity.

PS is a ubiquitous marker of microparticles arising from loss of phospholipid asymmetry during microparticle biogenesis. It was observed that significantly elevated numbers of PS$^+$ microparticles were in the total CD41a$^-$ microparticle population in multiple myeloma patients relative to healthy volunteers. Significantly higher PS$^+$ events in the CD138$^-$ microparticle sub-set in multiple myeloma patients (specifically, in de novo and PD) were also observed.

The results show that the presence of a 'dual positive' microparticle population (CD138$^+$/CD34$^+$/P-gp$^+$) provides a marker of disease progression and treatment responsiveness within individual patients, specifically in aggressive disease. It appears that CD138$^+$ cannot be considered a 'static' biomarker of multiple myeloma disease evolution. Whereas it plays an important role as a measure of tumor burden in responsive disease, its presence diminishes in an aggressive disease state.

Example 3

Samples were collected over a range of time for four additional patients across all disease states and their microparticles phoenotyped retrospectively for the presence P-gp, CD34 and CD138 according to the methods described in Example 1. The patients had the following clinical profiles (as determined by conventional blood tests):

MM34, Female

The patient had progressive, refractory multiple myeloma, and progressed through cyclophosphamide, velcade and dexamethasone, before passing away on 4th April 2014.

MM19, Male

The patient was diagnosed as having a stable multiple myeloma on 3 Sep. 2013, and treated with Thalidomide 50 mg (alternating with 100 mg at night together with Prednisone 50 mg) for 7 days each month. The patient's multiple myeloma became progressive.

MM79, Male

Kappa light chain multiple myeloma diagnosed in April 2014, followed by treatment with VCAT induction followed by ASCT and ThalVs Velcade maintenance. Responded well to treatment prior to partial relapse in October 2014.

MM49, Male

Diagnosed with IgA kappa myeloma in 2009, and responded well to treatment prior to partial relapse in May 2014. The results of the microparticle phenotyping are shown in Table 1 below.

TABLE 1

Levels of CD138$^-$/CD34$^+$/P-gp$^+$/CD41a$^-$ in patients

| Patient | Gender | Time line | Diagnosed response state | P-gp$^+$ CD34$^+$ (µl) CD41a$^-$ CD138$^-$ | P-gp$^+$ CD34$^+$ (µl) | P-gp$^+$ CD34$^+$ (µl) |
|---|---|---|---|---|---|---|
| MM34 | F | 29 Nov. 2013 | PD | 122 | 775.32 | 238.44 |
|  |  | 13 Dec. 2013 | PD | 152.17 | 788.73 | 208.99 |
|  |  | 17 Jan. 2014 | PD | 77.57 | 312.01 | 69.32 |
|  |  | 20 Feb. 2014 | PD | 61.68 | 130.66 | 207.84 |
|  |  | 11 Mar. 2014 | PD | 98.80 | 485.65 | 150.64 |
| MM19 | M | 30 Sep. 2013 | Stable | 38.17 | 177.54 | 43.40 |
|  |  | 4 Nov. 2013 | PD | 27.78 | 223.70 | 58.04 |
| MM79 | M | 1 May 2014 | PR | 4.95 | 9.57 | 22.38 |
|  |  | 10 Jun. 2014 | PR | 6.99 | 45.85 | 37.7 |
|  |  | 176/14 | PR | 8.59 | 40.28 | 119.42 |
|  |  | 7 Jul. 2014 | PR | 10.83 | 145.51 | 74.65 |
| MM49 | M | 3 Mar. 2014 | PR | 4.27 | 16.50 | 31.55 |
|  |  | 5 May 2014 | PR | 6.18 | 15.55 | 21.43 |

MM34 has consistently high levels of CD138–P-gp+CD34+ MPs, indicative of an aggressive/refractory cancer from which the patients does eventually die.
MM19 has a high level of CD138–P-gp+CD34+ MPs on 30 Sep. 2013, despite being diagnosed as stable, after which the disease becomes progressive 4 Nov. 2013.
MM79 has slowly increasing levels of CD138–P-gp+CD34+ MPs up until 7 Jul. 2014, after which point the patient was diagnosed with a partial relapse in October 2014.
MM49 has an increased level of CD138–P-gp+CD34+ MPs at 5 May 2014, after which the patient was suspected of relapsing on 13 May 2014.

We claim:

1. A method for the prognosis of a patient with a plasma cell neoplasm or suspected of having a plasma cell neoplasm, comprising isolating a sample comprising extracellular vesicles, or cells and extracellular vesicles, from said patient and determining the level of extracellular vesicles, or cells and extracellular vesicles, that are CD138$^-$ and P-glycoprotein$^+$ (CD138$^-$/P-gp$^+$), wherein the determining step comprises using an immunoaffinity method, wherein antibodies are directed towards a cell surface and/or microparticle-associated proteins; and wherein the immunoaffinity methods comprise using affinity pull-downs, Western blot analysis, dot blot analysis, radio-immune assays, flow cytometry, fluorescence activated cell sorting (FACS) analysis, magnetic beads, ELISA, immunofluorescence and/or affinity chromatography.

2. The method according to claim 1, wherein the plasma cell neoplasm is myeloma or multiple myeloma.

3. The method according to claim 1, wherein the sample is a blood-derived sample, a plasma sample, or a platelet-free plasma sample.

4. The method according to claim 1, wherein the extracellular vesicles, or the cells and extracellular vesicles, are also CD41a$^-$.

5. The method according to claim 1, wherein:
when the sample comprises extracellular vesicles, or cells and extracellular vesicles, that are CD138$^-$/P-gp$^+$ at a level that is higher than a reference control indicative of a subject that does not have a plasma cell neoplasm or has a remissive plasma cell neoplasm, a prognosis that the neoplasm is stable, progressive or refractory is determined;
when the sample comprises extracellular vesicles, or cells and extracellular vesicles, that are CD138$^-$/P-gp$^+$ at a level that is higher than a reference control indicative of a subject with a stable plasma cell neoplasm, a prognosis that the neoplasm is progressive or refractory is determined; or
when the sample comprises extracellular vesicles, or cells and extracellular vesicles, that are CD138$^-$/P-gp$^+$ at a level that is higher than a reference control indicative of a subject with progressive plasma cell neoplasm, a prognosis that the neoplasm is refractory is determined.

6. The method according to claim 1, wherein the extracellular vesicles, or the cells and extracellular vesicles, are also CD34$^+$.

7. The method according to claim 6, wherein:
when the sample comprises extracellular vesicles, or cells and extracellular vesicles, that are CD138$^-$/P-gp$^+$/CD34$^+$ at a level that is higher than a reference control indicative of a subject that does not have a plasma cell neoplasm or has a remissive plasma cell neoplasm, a prognosis that the neoplasm is stable, progressive or refractory is determined;
when the sample comprises extracellular vesicles, or cells and extracellular vesicles, that are CD138$^-$/P-gp$^+$/CD34$^+$ at a level that is higher than a reference control indicative of a subject with a stable plasma cell neoplasm, a prognosis that the neoplasm is progressive or refractory is determined; or
when the sample comprises extracellular vesicles, or cells and extracellular vesicles, that are CD138$^-$/P-gp$^+$/CD34$^+$ at a level that is higher than a reference control indicative of a subject with a progressive plasma cell neoplasm, a prognosis that the neoplasm is refractory is determined.

8. The method according to claim 1, wherein the extracellular vesicles, or the cells and extracellular vesicles, are also phosphatidylserine$^+$ (PS$^+$).

9. The method according to claim 8, wherein:
when the sample comprises extracellular vesicles, or cells and extracellular vesicles that are CD138$^-$/P-gp$^+$/CD34$^+$/PS$^+$ at a level that is higher than a reference control indicative of a subject that does not have a plasma cell neoplasm or a remissive plasma cell neoplasm, a prognosis that the neoplasm is stable, progressive or refractory is determined;
when the sample comprises extracellular vesicles, or cells and extracellular vesicles, that are CD138$^-$/P-gp$^+$/CD34$^+$/PS$^+$ at a level that is higher than a reference control indicative of a subject with a stable plasma cell neoplasm, a prognosis that the neoplasm is progressive or refractory is determined; or
when the sample comprises extracellular vesicles, or cells and extracellular vesicles, that are CD138$^-$/P-gp$^+$/CD34$^+$/PS$^+$ at a level that is higher than a reference control indicative of a subject with a progressive plasma cell neoplasm, a prognosis that the neoplasm is refractory is determined.

10. A method for monitoring the progression of a patient with a plasma cell neoplasm or suspected of having a plasma cell neoplasm, comprising isolating a sample comprising extracellular vesicles, or cells and extracellular vesicles, from said patient at at least two time points and determining the change in the level of extracellular vesicles, or cells and extracellular vesicles, that are CD138$^-$/P-gp$^+$, wherein the determining step comprises using an immunoaffinity method, wherein antibodies are directed towards a cell surface and/or microparticle-associated proteins; and wherein the immunoaffinity methods comprise using affinity pull-downs, Western blot analysis, dot blot analysis, radio-immune assays, flow cytometry, fluorescence activated cell sorting (FACS) analysis, magnetic beads, ELISA, immunofluorescence and/or affinity chromatography.

11. The method according to claim 10, wherein: when the level of extracellular vesicles, or cells and/or and extracellular vesicles, that are CD138$^-$/P-gp$^+$ increase between the at least two time points, a prognosis that the severity of the neoplasm is increasing is determined; or when the level of extracellular vesicles, or cells and extracellular vesicles, that are CD138$^-$/P-gp$^+$ decrease between subsequent time points, a prognosis that the severity of the neoplasm is decreasing is determined.

12. The method according to claim 4, wherein the plasma cell neoplasm is myeloma or multiple myeloma.

13. The method according to claim 4, wherein the sample is selected from the group consisting of a blood-derived sample, a plasma sample, a platelet-free plasma sample.

14. The method according to claim 10, wherein the extracellular vesicles, or the cells and extracellular vesicles, are also CD41a$^-$.

15. The method according to claim 4, wherein the extracellular vesicles, or the cells and extracellular vesicles, are also CD34$^+$.

16. The method according to claim 4, wherein the extracellular vesicles, or the cells and extracellular vesicles, are also phosphatidylserine$^+$ (PS$^+$).

17. The method according to claim 1, wherein the sample comprises cells that:
are produced in the bone marrow;
are hematopoietic stem cells;
originated from hematopoietic stem cells;
are myeloid progenitor cells;
originated from myeloid progenitor cells;
are lymphoid progenitor cells;
originated from lymphoid progenitor cells;
originated from B lymphocyte cells;
are plasma-like cells;
are neoplastic cells; or
are multiple myeloma cells.

18. The method according to claim 1, wherein the sample comprises extracellular vesicles that are derived from:
cells produced in the bone marrow;
cells that are hematopoietic stem cells;
cells that originated from hematopoietic stem cells;
cells that are myeloid progenitor cells;
cells that originated from myeloid progenitor cells;
cells that are lymphoid progenitor cells;
cells that originated from lymphoid progenitor cells;
cells that originated from B lymphocyte cells;
plasma-like cells;
neoplastic cells; or
multiple myeloma cells.

19. The method according to claim 1, wherein the sample comprises extracellular vesicles that are exosomes, microparticles, oncosomes, large oncosomes or migrasomes.

20. The method according to claim 4, wherein the sample comprises extracellular vesicles that are derived from:
cells produced in the bone marrow;
cells that are hematopoietic stem cells;
cells that originated from hematopoietic stem cells;
cells that are myeloid progenitor cells;
cells that originated from myeloid progenitor cells;
cells that are lymphoid progenitor cells;
cells that originated from lymphoid progenitor cells;
cells that originated from B lymphocyte cells;
plasma-like cells;
neoplastic cells; or
multiple myeloma cells.

* * * * *